US008993030B2

(12) United States Patent
Aldred et al.

(10) Patent No.: US 8,993,030 B2
(45) Date of Patent: Mar. 31, 2015

(54) LOW PH AERATED PRODUCTS

(75) Inventors: Deborah Lynne Aldred, Shambrook (GB); Andrew Richard Cox, Shambrook (GB)

(73) Assignee: Conopco, Englewood Cliffs, NJ (US)

( * ) Notice: Subject to any disclaimer, the term of this patent is extended or adjusted under 35 U.S.C. 154(b) by 2104 days.

(21) Appl. No.: 11/525,060

(22) Filed: Sep. 21, 2006

(65) Prior Publication Data

US 2007/0071865 A1    Mar. 29, 2007

(30) Foreign Application Priority Data

Sep. 23, 2005   (EP) .................................. EP05255943

(51) Int. Cl.
*A23L 1/00* (2006.01)
*A23J 3/20* (2006.01)
*A23L 1/212* (2006.01)
*A23G 9/38* (2006.01)
*A23G 9/46* (2006.01)
*A23L 1/24* (2006.01)
*C07K 14/37* (2006.01)

(52) U.S. Cl.
CPC ................. *A23L 1/2128* (2013.01); *A23G 9/38* (2013.01); *A23G 9/46* (2013.01); *A23L 1/24* (2013.01); *C07K 14/37* (2013.01)
USPC ........... 426/564; 426/565; 426/329; 426/569; 426/590; 426/594; 426/597; 426/599; 426/601; 426/656

(58) Field of Classification Search
None
See application file for complete search history.

(56) References Cited

U.S. PATENT DOCUMENTS

| | | | |
|---|---|---|---|
| 2,604,406 A | 7/1952 | Blihovde | |
| 2,844,470 A * | 7/1958 | Akerboom et al. | ........... 426/116 |
| 2,937,093 A | 5/1960 | Gorman et al. | |
| 2,970,917 A | 2/1961 | Melnick | |
| 3,266,214 A | 8/1966 | Kramme | |
| 3,346,387 A | 10/1967 | Moncrieff et al. | |
| 3,914,441 A | 10/1975 | Finney et al. | |
| 3,946,122 A | 3/1976 | Scharp | |
| 4,012,533 A | 3/1977 | Jonas | |
| 4,066,794 A | 1/1978 | Schur | |
| 4,146,652 A | 3/1979 | Kahn et al. | |
| 4,305,964 A | 12/1981 | Moran et al. | |
| 4,325,980 A | 4/1982 | Rek et al. | |
| 4,425,369 A | 1/1984 | Sakamoto et al. | |
| 4,542,035 A | 9/1985 | Huang et al. | |
| 4,627,631 A | 12/1986 | Sherman | |
| 4,627,983 A | 12/1986 | Scharf et al. | |
| 4,629,628 A | 12/1986 | Negro | |
| 4,668,519 A | 5/1987 | Dartey et al. | |

(Continued)

FOREIGN PATENT DOCUMENTS

| CA | 1094866 | 10/2003 |
|---|---|---|
| CA | 1218557 | 11/2004 |

(Continued)

OTHER PUBLICATIONS

Hakanpaa et al. ("Atomic Resolution Structire of the HFBII Hydrophobin, a Self-assenbling Amphiphile" 2004. The Journal of Biological Chemistry vol. 279, No. 1 534-539.*

(Continued)

*Primary Examiner* — Felicia King
(74) *Attorney, Agent, or Firm* — Alan A. Bornstein

(57) ABSTRACT

An aerated composition having a pH of less than 5.5 is provided, which composition comprises hydrophobin.

22 Claims, 7 Drawing Sheets

(56) References Cited

U.S. PATENT DOCUMENTS

| | | |
|---|---|---|
| 4,869,915 A | 9/1989 | Inayoshi et al. |
| 4,874,627 A | 10/1989 | Greig et al. |
| 4,946,625 A | 8/1990 | O'Lenick |
| 4,954,440 A | 9/1990 | Johal et al. |
| 4,960,540 A | 10/1990 | Friel et al. |
| 5,084,295 A | 1/1992 | Whelan et al. |
| 5,104,674 A | 4/1992 | Chen et al. |
| 5,202,147 A | 4/1993 | Traska et al. |
| 5,208,028 A | 5/1993 | Clement et al. |
| 5,215,777 A | 6/1993 | Asher et al. |
| 5,336,514 A | 8/1994 | Jones et al. |
| 5,393,549 A | 2/1995 | Badertscher et al. |
| 5,397,592 A | 3/1995 | Vermaas et al. |
| 5,436,021 A | 7/1995 | Bodor et al. |
| 5,486,372 A | 1/1996 | Martin et al. |
| 5,536,514 A | 7/1996 | Bishay et al. |
| 5,624,612 A | 4/1997 | Sewall et al. |
| 5,681,505 A | 10/1997 | Phillips et al. |
| 5,738,897 A | 4/1998 | Gidley |
| 5,770,248 A | 6/1998 | Leibfred et al. |
| 5,980,969 A * | 11/1999 | Mordini et al. .............. 426/597 |
| 6,096,867 A | 8/2000 | Byass et al. |
| 6,187,365 B1 | 2/2001 | Vaghela et al. |
| 6,238,714 B1 | 5/2001 | Binder et al. |
| 6,284,303 B1 | 9/2001 | Rowe et al. |
| 6,497,913 B1 | 12/2002 | Gray et al. |
| 6,579,557 B1 | 6/2003 | Benjamins et al. |
| 6,685,977 B1 | 2/2004 | Asano et al. |
| 6,914,043 B1 | 7/2005 | Chapman et al. |
| 7,338,779 B1 | 3/2008 | Nakari-Setala et al. |
| 8,038,740 B2 | 10/2011 | Subkowski et al. |
| 8,178,151 B2 | 5/2012 | Bramley et al. |
| 8,206,770 B2 | 6/2012 | Aldred et al. |
| 8,216,624 B2 | 7/2012 | Berry et al. |
| 2001/0048962 A1 | 12/2001 | Fenn et al. |
| 2002/0085987 A1 | 7/2002 | Brown et al. |
| 2002/0155208 A1 | 10/2002 | Benjamins et al. |
| 2002/0182300 A1 | 12/2002 | Groh et al. |
| 2002/0197375 A1 | 12/2002 | Adolphi et al. |
| 2003/0087017 A1 | 5/2003 | Hanselmann et al. |
| 2003/0099751 A1 | 5/2003 | Aldred et al. |
| 2003/0134025 A1 | 7/2003 | Vaghela et al. |
| 2003/0148400 A1 | 8/2003 | Haikara et al. |
| 2003/0166960 A1 | 9/2003 | DeVocht et al. |
| 2003/0175407 A1 | 9/2003 | Kunst et al. |
| 2003/0190402 A1 | 10/2003 | McBride |
| 2004/0109930 A1 | 6/2004 | Hooft et al. |
| 2004/0185162 A1 | 9/2004 | Finnigan et al. |
| 2005/0037110 A1 | 2/2005 | Windhab et al. |
| 2005/0123666 A1 | 6/2005 | Vaghela et al. |
| 2005/0123668 A1 | 6/2005 | Kodali et al. |
| 2005/0129810 A1 | 6/2005 | Lindner et al. |
| 2005/0193744 A1 | 9/2005 | Cockings et al. |
| 2005/0220961 A1 | 10/2005 | Cox et al. |
| 2006/0024417 A1 | 2/2006 | Berry et al. |
| 2006/0024419 A1 | 2/2006 | Berry et al. |
| 2007/0014908 A1 | 1/2007 | Bramley et al. |
| 2007/0286936 A1 | 12/2007 | Bramley et al. |
| 2007/0298490 A1 | 12/2007 | Sweigard et al. |
| 2008/0187633 A1 | 8/2008 | Cox |
| 2008/0254180 A1 | 10/2008 | Windhab et al. |
| 2008/0305237 A1 | 12/2008 | Beltman et al. |
| 2009/0136433 A1 | 5/2009 | Subkowski et al. |

FOREIGN PATENT DOCUMENTS

| | | | |
|---|---|---|---|
| CA | 2575325 | 2/2006 | |
| DE | 29715519 | 1/1998 | |
| EP | 216270 | 4/1987 | |
| EP | 0274348 | 7/1988 | |
| EP | 0285198 | 10/1988 | |
| EP | 0322952 A2 | 7/1989 | |
| EP | 0426211 | 5/1991 | |
| EP | 0469656 | 2/1992 | |
| EP | 0521543 | 6/1992 | |
| EP | 747301 | 11/1996 | |
| EP | 0477825 B1 | 12/1996 | |
| EP | 0775444 A1 | 5/1997 | |
| EP | 0930017 | 7/1999 | |
| EP | 1074181 A1 | 2/2001 | |
| EP | 919134 | 11/2001 | |
| EP | 0771531 B1 | 9/2002 | |
| EP | 1284106 | 2/2003 | |
| EP | 995685 | 4/2003 | |
| EP | 077969 B1 * | 7/2003 | ............. A23C 9/154 |
| EP | 0777969 | 7/2003 | |
| EP | 1327390 | 7/2003 | |
| EP | 1520483 | 4/2005 | |
| EP | 1520484 | 4/2005 | |
| EP | 1520485 | 4/2005 | |
| EP | 1557092 | 7/2005 | |
| EP | 1449441 | 12/2005 | |
| EP | 1621084 | 2/2006 | |
| EP | 1623631 | 4/2007 | |
| EP | 1849461 A1 | 10/2007 | |
| EP | 1938697 | 7/2008 | |
| EP | 1061006 | 8/2008 | |
| EP | 1400486 | 3/2011 | |
| GB | 459583 | 1/1937 | |
| GB | 1556297 | * 11/1979 | ................ A23J 3/00 |
| JP | 50-5596 | 1/1975 | |
| JP | 61219342 | 9/1986 | |
| JP | 3244348 A | 10/1991 | |
| JP | 5503426 | 6/1993 | |
| JP | 08500486 | 1/1996 | |
| JP | 2002508303 | 12/1998 | |
| JP | 2005278484 | 10/2005 | |
| WO | WO9013571 | 11/1990 | |
| WO | WO9222581 | 12/1992 | |
| WO | WO9403617 | 2/1994 | |
| WO | 94/13154 | 6/1994 | |
| WO | WO9412050 | 6/1994 | |
| WO | WO9523843 | 9/1995 | |
| WO | WO9611586 | 4/1996 | |
| WO | WO9621362 | 7/1996 | |
| WO | WO 96/39878 | 12/1996 | |
| WO | WO 96/41882 | 12/1996 | |
| WO | WO9804699 | 2/1998 | |
| WO | WO9937673 | 7/1999 | |
| WO | WO 99/54725 | 10/1999 | |
| WO | 00/22936 | 4/2000 | |
| WO | WO 00/38547 | 7/2000 | |
| WO | WO 00/53027 | 9/2000 | |
| WO | WO 00/58342 | 10/2000 | |
| WO | WO 01/14521 | 3/2001 | |
| WO | WO0135756 A1 | 5/2001 | |
| WO | WO 01/57076 | 8/2001 | |
| WO | WO 01/74864 | 10/2001 | |
| WO | WO 01/83534 | 11/2001 | |
| WO | WO0184945 A1 | 11/2001 | |
| WO | WO03015530 A1 | 2/2003 | |
| WO | WO03051136 A1 | 6/2003 | |
| WO | WO 03/053383 | 7/2003 | |
| WO | WO03053883 | 7/2003 | |
| WO | 03/096821 | 11/2003 | |
| WO | WO 2005/058055 | 6/2005 | |
| WO | WO2005058067 A1 | 6/2005 | |
| WO | 2005/102067 | 11/2005 | |
| WO | 2005/113387 | 12/2005 | |
| WO | WO 2006/010425 | 2/2006 | |
| WO | WO 2006/010426 | 2/2006 | |
| WO | WO 2007/039065 | 4/2007 | |
| WO | WO2008031796 A1 | 3/2008 | |
| WO | WO 2009/047657 | 4/2009 | |
| WO | WO2010067059 A1 | 6/2010 | |

OTHER PUBLICATIONS

Light "Modified Starches: Why, What, Where and How" 1990 The American Association of Cereal Chemists vol. 35 No. 11 1-20 pages.*

International Search Report International application No. PCT/EP2006/008992 mailed Dec. 7, 2006.

(56) References Cited

OTHER PUBLICATIONS

Russo et al., "The surface activity of the phytotoxin cerato-ulmin", 1982 National Research Council of Canada.
Teodora Gliga, article available on the Internet at least as of May 29, 2007 regarding hydrophobins.
Co-pending application No. WO2006/010425 dated Feb. 2, 2006.
European Search Report EP 05255943 dated Dec. 29, 2005.
European Search Report EP 05255944 dated Feb. 17, 2006.
European Search Report EP 05256960 dated Mar. 15, 2006.
Database WPI, Section Ch, Week 200444, Derwent Publications Ltd., London, GB; Class B04, AN 2004-465457, XP002313777 & KR 2004 018 844 A (Kim), Mar. 4, 2004.
Scholmeijer et al., "Fungal Hydrophobins in Medical and Technical Applications", Appllied Microbiology and Biotechnology, Springer Verlag, Berlin, DE, vol. 56, No. ½, Jul. 2001, pp. 1-8, XP001120015.
Woesten et al., "Hydrophobins, the fungal coat unraveled", Biochimica et Biophysica Acta. Mr. Reviews on Biomembranes, Elsevier, Amsterdam, NL, vol. 1469, No. 2, Sep. 18, 2000, pp. 79-86, XP004281756.
Van der Werf, "Surface Active Proteins", Leads in Life Science, Jul. 2000:5.
Office Action dated Oct. 19, 2009 for Aldred et al., U.S. Appl. No. 11/168,214, filed Jun. 27, 2005.
Co-pending application Aldred et al., U.S. Appl. No. 12/287,957, filed Oct. 15, 2008.
Co-pending application Aumaitre et al., U.S. Appl. No. 12/409,549, filed Mar. 24, 2009.
International Search Report International Application No. PCT/EP2006/008989 completed Nov. 24, 2006.
International Search Report International Application No. PCT/EP2006/008993 completed Jan. 5, 2007.
Penttila et al., "Molecular Biology of *Trichoderma* and Biotechnological Applications", Handbook of Fungal Biotechnology, 2$^{nd}$ Ed., vol. 20, 2004, pp. 413-427.
Office Action dated Dec. 30, 2010 for Bramley et al., U.S. Appl. No. 11/639,851, filed Dec. 15, 2006.
Office Action dated Dec. 29, 2010 for Burmester et al., U.S. Appl. No. 12/002,684, filed Dec. 18, 2007.
Office Action dated Oct. 5, 2010 for Aldred et al., U.S. Appl. No. 11/524,977, filed Sep. 21, 2006.
Office Action dated Sep. 13, 2010 for Cox et al., U.S. Appl. No. 11/524,675, filed Sep. 21, 2006.
Office Action dated Dec. 7, 2010 for Cox et al., U.S. Appl. No. 11/699,601, filed Jan. 30, 2007.
Office Action dated Oct. 8, 2010 for Cox, U.S. Appl. No. 11/699,602, filed Jan. 30, 2007.
Bay, "La Cucina Italiana", Pozzo Gros Monti S.p.A., 2002, p. 1233.
Berolzheimer, "Culinary Arts Institute Encyclopedic Cookbook", 1988, p. 648.
Nestle Research Center, Search Proteins Matching the Sequence Pattern used for the Hydrophpobin Definition in patent EP 1926399 B1, Oct. 16, 2009, 3 pp.
Neste Research Center, Adsorption of different proteins to Teflon sheets: Experimental Results, Nov. 16, 2009, Dr. E. Kolodziejcxzyk, 10 pp.
Quintas,"Rheology of supersaturated sucrose solutions", Elsevier, Journal of Food Engineering 77 (2006), pp. 844-852.
Whitcomb, "Rheology of Guar Solutions", 1980 John Wiley & Sons, Inc., Journal of Applied Polymer Science, vol. 25, pp. 2815-2827 (1980).
Jan. 1, 2005, Fats Oils Fatty Acids Triglycerides, Scientific Psychic, 1-4.
Oct. 16, 2009, Search proteins matching the sequence pattern used for the hydrophobin definition in patent EP 1 926 399 B1, Nestle Research Center, 1-3.
Feb. 25, 2008, Research pushes the right buttons, mushrooms are the new fat, University of Birmingham, 1-2.
Arbuckle, Jan. 1, 1972, Ice Cream, Ice Cream 2nd Ed 1972 pp. 35 266 284-285, 2nd Edition, 35, 266, 284-285.
Arbuckle, 1972, Ice Cream, Ice Cream, 2nd Ed., 265, Avi Publishing Company.
Arbuckle, 1972, Ice Cream, Ice Cream, 2nd, 31.
Askolin, et al., Jan. 10, 2006, Interaction & comparison of a Class I Hydrophobin from schizophyllum commune & Class II Hydro form *Trichoderma reesei*, Biomacromolecules, 7, 1295-1301.
Berolzheimer, Jan. 1, 1988, Culinary Arts Institute Encyclopedic Cookbook, Culinart Arts Institute, 648.
Chaisalee, et al., Oct. 1, 2003, Mechanism of Antifoam Behavior of Solutions of Nonionic Surfactants Above the Cloud Point, Journal of Surfactants & Detergents, 6, No. 4, 345-351.
Chakraborty, et al., Jan. 1, 1972, Stabilization of Calcium Sensitive Plant Proteins by k-Carrageenan, Journal of Food Science, 37, 719-721.
Cheer, et al., Jan. 1, 1983, Effects of Sucrose on the Rheological Behavior of Wheat Starch Pastes, Journal of Applied Polymer Science, 28, 1829-1836.
CP Kelco US Inc., Apr. 17, 2007, Certificate of Analysis for Keltrol RD, CP Kelco, 1.
CRC, Jan. 1, 2008, Fennema's Food Chemistry, CRC Press, 4th Ed., pp. 727-728, Taylor & Francis Group.
Cruse, May 26, 1970, Whipped Soup is Tasty, St. Petersberg Independant, ., B-4.
Davis, et al., Jan. 1, 2001, Application of foaming for the recovery of surfactin from *B. subtilis* ATCC 21332 cultures, Enzyme & Microbial Technology, 28, 346-354.
De Vocht et al., Apr. 1998, Structural Characterization of the Hydrophobin SC3, as a Monomer and after Self-Assembly at Hydrophobic/Hydrophilic Interfaces, Biophysical Journal, 74, 2059-2068.
Dickinson, Dec. 2, 2010, Mixed biopolymers at interfaces: Competitive adsorption and multilayer structures, Food Hydrocolloids, 25, 1966-1983.
Fellows, 2000, Principles and Practice, Food processing technology, 2nd, 83, 140, 429, Foodhead Publishing.
Fox, 1992, Analytical methods for Milk Proteins, Advanced Dairy Chemistry 1: Proteins, 1, 1, 6-7.
Goh, Apr. 8, 2002, Applications and Uses of Palm and Palm Kernel Oils, Malaysian Oil Science and Technology, 11, 46-50.
Graham et al, Jul. 3, 1979, Proteins at Liquid Interfaces, Journal of Colloid and Interface Science, 70, 415-426.
Grant, Jan. 1, 1987, Grant & Hackh's Chemical Dictionary, McGraw-Hill, 5th Ed, 212.
Guinee et al., 2004, Salt in Cheese: Physical, Chemical and Biological Aspects, Cheese: Chemistry, Physics and Microbiology, vol. 1, 3rd ed., pp. 207-259.
Holmes, et al., Oct. 10, 2006, Evaluation of antifoams in the expression of a recombinant FC fusion protein in shake flask cultures, Microbial Cell Factories, 5, No. 1, p. 30.
Hui, Jan. 1, 1992, Encyclopedia of Food Science & Tehcnology, John Wiley & Sons, 1, 204-210.
Hung, et al., Aug. 20, 2007, Cloud-point extraction of selected polycyclic aromatic hydrocarbons by nonionic surfactants, Separation & Purification Tech, 57, 1-10.
Hunter, et al., Jan. 1, 2008, The role of particles in stabilising foams and emulsions, Advances in Colloid & Interface Science, 137, 57-81.
Katzbauer et al, Jun. 19, 1997, Properties and applications of xanthan gum, Polymer Degradation and Stability, vol. 59, 81-84, Elsevier.
Kilkast et al., Jun. 20, 2002, Sensory perception of creaminess and its relationship with food structure, Food Quality and Preference, 13, 609-623.
Lambou et al., 1973, Whey Solids as Agricultural Foam Stabilizers, Jr. of Agr. and Food Chemistry, 21 No. 2, 257-263.
Lumsdon, et al., Sep. 1, 2005, Adsorption of hydrophobin proteins at hydrophobic & hydrophilic interfaces, Colloids & Surfaces, 44, 172-178.
Marshall, Jan. 1, 2003, Ice Cream, Springer, 6th Ed, 70-73.
Martin, et al., Jan. 14, 2000, Sc30 Hydrophobin Organization in Aqueous Media & Assembly onto Surfaces as Mediated by Assoc Polysaccharide Schizophyllan, Biomacromolecules, 1, 49-60.
Mathlouthi, et al., Jan. 1, 1995, Rheological properties of sucrose solutions and suspensions, Sucrose Properties & Applic, 126-154.
McGregor, et al., Jan. 1, 1988, Antifoam effects on ultrafiltration, Biotechnology & Bioengineering, 31, No. 4, 385-389.

(56) References Cited

OTHER PUBLICATIONS

Miquelim et al., 2010, pH Influence on the stability of foams with protein-polysaccharide complexes at their interfaces, Food Hydrocolloids, 24, No. 4, 398-405.

Nakari-Setala, et al., May 26, 1997, Differential expression of the vegetative and spore-bound hydrophobins of *Trichoderma reesei*, Eur J. Biochem, 248, 415-423.

Patino and Pilosof, 2011, Protein-polysaccharide interactions at fluid interfaces, Food Hydrocolloids, 25, 1925-1937.

Quintas, et al., Jan. 1, 2006, Rheology of superstaurated sucrose solutions, Journal of Food Engineering, 77, 844-852.

Sanderson, 1981, Applications of Xanthan Gum, British Polymer Jr., 13, 71-75.

Schmitt, Feb. 27, 2012, Declaration of Christophe Schmitt, Declaration of Christophe Schmitt, ., 1-4.

Sienkiewicz, Jan. 1, 1990, Whey and Whey Utilization, Verlag Th Mann, 2nd Ed, 82-83.

Swern, Jan. 1, 1979, Baileys Industrial Oil and Fat Products, John Wiley & Sons, 1, 369.

Takai, et al., Jan. 1, 1978, Cerato-ulmin, a wilting toxin of *Ceratocystis ulmi*: isolation & some properties of cerato-ulmin from the culture of *C. ulmi*, Phytopath, 91, 129-146.

Talbot, et al., Jun. 1, 1996, MPG1 encodes a fungal hydrophobin involved in surface interactions during infection-related develop of *Magnaporthe grisea*, Plant Cell, 8, 985-999.

Temple, 2000, Biological Roles for cerato-Ulmin, a Hydrophobin secreted by the elm pathogens, *Opthiostoma ulmi* and *O. novo-ulmi*, Micological Society of America, 92, 1-9 Abstract.

Wang et al, May 31, 2004, Protease a Stability of Beer Foam II, China Acadmic Journal Electronic Publishing House, ., 11-15.

Arbuckle, 1972, Ice Cream, Ice Cream, 2nd Edition, pp. 15, 18, 35, 61, 65.

Kinderlerer, 1997, *Chrysosporium* species, potential spoilage organisms of chocolate, Journal of Applied Microbiology, vol. 83, pp. 771-778.

Pardun, 1977, Soy Protein Preparations as Antispattering Agents for Margarine, Fette Seifen Anstrichmittel, vol. 79, No. 5, pp. 195-203, Abstract.

Samsudin, May 26, 2010, Low-Fat Chocolate Spread Based on Palm Oil, Malasyian Palm Oil Board, ., pp. 27-30.

Scott et al., 1983, Influence of Temperature on the Measurement of Water Activity of Food and Salt Systems, Journal of Food Science, vol. 48, pp. 552-554.

Co-Pending application Mitchell et al., U.S. Appl. No. 13/498,157, filed Mar. 26, 2012.

Co-Pending application Aldred et al., U.S. Appl. No. 13/378,143, filed Feb. 10, 2012.

Co-Pending application Hedges et al., U.S. Appl. No. 12/636,157, filed Dec. 11, 2009.

Co-Pending application Cox et al., U.S. Appl. No. 12/682,717, filed Apr. 12, 2010.

Co-Pending application Aldred et al., U.S. Appl. No. 12/788,395, filed May 27, 2010.

Kloek, et al., Feb. 2, 2001, Effect of Bulk and Interfacial Rheological Properties on Bubble Dissolution, Journal of Colloid & Interface Sc, 237, 158-166.

Russo, et al., Jan. 1, 1982, Surface activity of the phytotoxin cerato-ulmin, Natl Research Council of Canada, 60, 1414-1422.

Stringer, et al., Feb. 1, 1993, Cerato-ulmin a toxin involved in dutch elm disease is a fungal hydrophobin, Plant Cell, 145-146.

Van Der Werf, Jan. 1, 2000, Green coatings healthy foods and drug targeting, Leads in Life Science, 5, 1.

Wessels, et al., Jan. 1, 1996, Fungal hydrophobins proteins that function at an interface, Trends in Plant Science, 1, No. 1, 9-15.

2012, West Search History for U.S. Appl. No. 12/636,157, Carbohydrates, 1-29.

Formo et al., 1979, Bailey Industrial Oil and Fat Products, Bailey's Industrial Oil and Fat Products, vol. 1, 4th edition, pp. 317, 326, 377, 382, 398.

Jackson, Apr. 16, 2008, Hard or Soft, red or White—or a blend?, Flour Power, pp. 1-4.

Kododziejcxzyk, Nov. 16, 2009, Adsortion of different proteins to Teflon sheets: Experimental Results, Nestle Research Center, 1-10.

Wosten, et al., Nov. 1, 1993, Interfacial self-assembly of a fungal hydrophobin into a hydrophobic rodlet layer, Plant Cell, 5, 1567-1574.

Response to Notice of Opposition, dated Oct. 29, 2010—Nestec S.A./Unilever N.V. (EP1926399).

Co-Pending application Cox et al., U.S. Appl. No. 13/585,257, filed Aug. 14, 2012.

Linder et al., "Hydrophobins: the protein-amphiphiles of filamentous fungi", FEMS Microbiology Reviews 29 (2005), 877-896, reported to be first published online Mar. 5, 2005.

deVocht et al., "Structural Characterization of the Hydrophobin SC3, as a Monomer and after Self-Assembly at Hydrophobic/Hydrophilic Interfaces", Biophys. J. 74:pp. 2059-2068, Apr. 1998.

Russo et al., "The surface activity of the phytotoxin cerato-ulmin", 1982, Can J. Bot., 60, p. 1414, National Research Council of Canada.

Murray, "Stabilization of bubbles and foams", Current Opinion in Colloid & Interface Science 12 (2007) 232-241.

Minor et al., "Preparation and sensory perception of fat-free foams—effect of matrix properties and level of aeration", International Journal of Food Science and Technology, 2009, 44, 735-747.

Kilcast et al., "Sensory perception of creaminess and its relationship with food structure", Food Quality and Preference 13 (2002) 609-623.

Office Action dated Jun. 10, 2009 for Cox et al., U.S. Appl. No. 11/699,601, filed Jan. 30, 2007.

Office Action dated Jun. 26, 2009 for Cox et al., U.S. Appl. No. 11/699,602, filed Jan. 30, 2007.

Guner et al., "Production of yogurt ice cream at different acidity", International Journal of Food Science and Technology, 2007, 42, 948-952.

McCabe et al., "Secretion Cryparin, a Fungal Hydrophobin", Applied and Environmental Microbiology, Dec. 1999, vol. 65, No. 12, pp. 5431-5435.

Talbot, "Aerial morphogenesis: Enter the Chaplin", Current Biology, vol. 13, Sep. 2003, R696-R698.

Calonje et al., "Properties of a hydrophobin isolated from the mycoparasitic fungus *Verticillium fungicola*", Can. J. Microbiol., 2002, 48: pp. 1030-1034.

Office Action dated Mar. 10, 2009 for Berry et al., U.S. Appl. No. 11/168,209, filed Jun. 27, 2005.

Office Action dated Mar. 16, 2009 for Aldred et al., U.S. Appl. No. 11/168,214, filed Jun. 27, 2005.

Linder et al., "The Hydrophobins HFBI and HFBII from *Trichoderma reesi* Showing Efficient Interactions with Nonionic Surfactants in Aqueous Two-Phase Systems", Biomacromolecules 2001, 2, 511-517.

Strimger et al., "Cerato-ulmin, a Toxin Involved in Dutch Elm Disease, is a Fungal Hydrophobin", The Plant Cell, Feb. 1993, pp. 145-146.

Linder et al., "Hydrophobins: the protein-amphiphiles of filamentous fungi", FEMS Microbiology Reviews 29 (2005) 877-896.

Wessels, "Hydrophobins: Proteins that Change the Nature of the Fungal Surface", Advances in Microbial Physiology, Academic Press, London, GB, vol. 38, No. 38, 1997, pp. 1-45.

Wosten, "Hydrophobins: Multipurpose Proteins", Annu. Rev. Microbiol. 2001, 55:625-46.

deVocht et al., "Structural Characterization of the Hydrophobin SC3, as a Monomer and after Self-Assembly at Hydrophobic/Hydrophilic Interfaces", Biophys. J. 74: pp. 2059-2068, Apr. 1998.

Collen et al., "A novel two-step extraction method with detergent/polymer systems for primary recovery of the fusion protein endoglucanase I-hydrophobin I", 2002 Biochim Biophys. Acta. 1569: pp. 139-150.

Calonje et al., "Properties of a hydrophobin isolated from the mycoparasitic fungus *Verticillium fungicola*", Can. J. Microbiol. 48: pp. 1030-1034, 2002.

Askolin et al., "Overproduction, purification, and characterization of the *Trichoderma reesei* hydrophobin HFBI", 2001, Appl. Microbiol. Biotechnol. 57: pp. 124-130.

(56) References Cited

OTHER PUBLICATIONS

De Vries et al., "Identification and characterization of a tri-partite hydrophobin from *Claviceps fusiformis*", 1999, Eur. J. Biochem. 262: pp. 377-385.
Talbot, 2001 "7 Fungal Hydrophobins", The Mycota: a Comprehensive Treatise on fungi as Experimental systems for basic and applied research, Howard and Gow (Eds.), vol. 7: "Biology of the fungal cell" Springer-Verlag, Berline and Heidelbert GmbH and Co., pp. 145-159, 2001.
Wessels, "Fungal hydrophobins: proteins that function at an Interface", Trends in Plant Science, Elsevier Science, Oxford GB, vol. 1, Jan. 1996, pp. 9-15.
Kloek et al., "Effect of Bulk and Interfacial Rheological Properties on Bubble Dissolution", Journal of Colloid and Interface Science 237, 158-166 (2001).
Soukoulis et al., "Impact of the acidification process, hydrocolloids and protein fortifiers on the physical and sensory properties of frozen yogurt", International Journal of Dairy Technology, vol. 61, No. 2, May 2008.
Cox et al., "Surface Properties of Class II Hydrophobins from *Trichoderma reesei* and Influence on Bubble Stability", Langmuir 2007, 23, 7995-8002.
Cox et al., "Exceptional stability of food foams using class II Hydrophobin HFBII", Food Hydrocolloids 23, (2009), 366-376.
Tchuenbou-Magaia et al., "Hydrophobins stabilized air-filled emulsions for the food industry", Food Hydrocolloids 23 (2009), 1877-1885.
Murray et al., "Foam stability: proteins and nanoparticles", Colloid & Interface Science 9 (2004) 314-320.
Kershaw et al., "Hydrophobins and Repellents: Proteins with Fundamental Roles in Fungal Morphogenesis", Fungal Genetics and Biology 23, 18-33 (1998).
Gilga, article available on Internet at least as of May 29, 2007 regarding hydrophobins (original plus English language translation), 2007.
Co-pending application Cox et al., U.S. Appl. No. 11/699,601, filed Jan. 30, 2007.
Co-pending application Bramley et al., U.S. Appl. No. 11/639,851, filed Dec. 15, 2006.
Co-pending application Berry et al., U.S. Appl. No. 11/168,209, filed Jun. 27, 2005.
Co-pending application Cox et al., U.S. Appl. No. 11/524,675, filed Sep. 21, 2006.
Co-pending application Aldred et al., U.S. Appl. No. 11/524,977, filed Sep. 21, 2006.
Co-pending application Aldred et al., U.S. Appl. No. 11/168,214, filed Jun. 27, 2005.
Co-pending application Burmester et al., U.S. Appl. No. 12/002,684, filed Dec. 18, 2007.
Office Action dated Jun. 26, 2009 for Cox, U.S. Appl. No. 11/699,602.
Office Action dated Mar. 17, 2010 for Cox, U.S. Appl. No. 11/699,602.
Office Action dated Jun. 10, 2009 for Cox et al., U.S. Appl. No. 11/699,601.
Office Action dated Dec. 28, 2009 for Cox et al., U.S. Appl. No. 11/699,601.
Office Action dated May 18, 2010 for Cox et al.., U.S. Appl. No. 11/699,601.
Office Action dated Feb. 18, 2009 for Cox, U.S. Appl. No. 11/524,675.
Office Action dated Dec. 18, 2009 for Cox, U.S. Appl. No. 11/524,675.
Office Action dated Jan. 4, 2006 for Aldred et al., U.S. Appl. No. 11/168,214.
Office Action dated Aug. 8, 2006 for Aldred et al., U.S. Appl. No. 11/168,214.
Office Action dated Feb. 12, 2007 for Aldred et al., U.S. Appl. No. 11/168,214.
Office Action dated Sep. 25, 2007 for Aldred et al., U.S. Appl. No. 11/168,214.
Office Action dated Jul. 14, 2008 for Aldred et al., U.S. Appl. No. 11/168,214.
Interview Summary dated Jul. 15, 2008 for Aldred et al., U.S. Appl. No. 11/168,214.
Cox Declaration dated Jan. 13, 2009 for Aldred et al., U.S. Appl. No. 11/168,214.
Amendment dated Jan. 14, 2009 for Aldred et al., U.S. Appl. No. 11/168,214.
Amendment dated Mar. 18, 2010 for Aldred et al., U.S. Appl. No. 11/168,214.
Cox Declaration dated Mar. 18, 2010 for Aldred et al., U.S. Appl. No. 11/168,214.
Cox Declaration ($2^{nd}$) dated Mar. 18, 2010 for Aldred et al., U.S. Appl. No. 11/168,214.
Office Action dated Jun. 25, 2010 for Aldred et al., U.S. Appl. No. 11/168,214.
Office Action dated Sep. 8, 2006 for Berry et al., U.S. Appl. No. 11/168,209.
Office Action dated Apr. 17, 2007 for Berry et al., U.S. Appl. No. 11/168,209.
Office Action dated Jan. 18, 2008 for Berry et al., U.S. Appl. No. 11/168,209.
Interview Summary dated Jul. 15, 2008 for Berry et al., U.S. Appl. No. 11/168,209.
Amendment dated Jul. 18, 2008 for Berry et al., U.S. Appl. No. 11/168,209.
Cox Declaration dated Jan. 12, 2009 for Berry et al., U.S. Appl. No. 11/168,209.
Amendment dated Jan. 23, 2009 for Berry et al., U.S. Appl. No. 11/168,209.
Office Action dated Dec. 18, 2009 for Berry et al., U.S. Appl. No. 11/168,209.
Interview Summary dated Jan. 26, 2010 for Berry et al., U.S. Appl. No. 11/168,209.
Cox Declaration dated May 18, 2010 for Berry et al., U.S. Appl. No. 11/168,209.
Office Action dated Jun. 17, 2010 for Berry et al., U.S. Appl. No. 11/168,209.
Office Action dated Dec. 1, 2009 for Bramley et al., U.S. Appl. No. 11/639,851.
Office Action dated Jun. 23, 2010 for Bramley et al., U.S. Appl. No. 11/639,851.
Office Action for Aldred et al., U.S. Appl. No. 11/524,977 dated Feb. 20, 2009.
Interview Summary for Aldred et al., U.S. Appl. No. 11/524,977 dated Jul. 1, 2009.
Supplement Amendment for Aldred et al., U.S. Appl. No. 11/524,977 dated Aug. 26, 2009.
Supplemental Amendment for Aldred et al., U.S. Appl. No. 11/524,977 dated Sep. 18, 2009.
Office Action for Aldred et al., U.S. Appl. No. 11/524,977 dated Dec. 14, 2009.
Communication of a Notice of Opposition—Nestec S.A./Unilever N.V. (EP 1926399), 2009.
Cover sheet and first page of D5 of Opposition—Nestec S.A./Unilever N.V. (EP 1926399), Arora et al. 2004.
PCT International Preliminary Report on Patentability International Application No. PCT/EP2006/008993 dated Dec. 17, 2007.
Communication pursuant to Article 94(3) EPC, Application No. 06 805 732.2-1221 dated Jul. 1, 2008.
Annex International Preliminary Report on Patentability, International Application No. PCT/EP2006/008993.
Wosten et al., "Interfacial self-assembly of a hydrophobin into an emphipathic peotein membrane mediates fungal attachment to hydrophobic surfaces", The EMBO Journal, vol. 13, No. 24, pp. 5848-5854, 1994.
Dr. E. Kolodziejcxzyk, "Adsorption of different proteins to Teflon sheets: Experimental results", Nestle Research Center, Nov. 16, 2009.
Damodaran, "Adsorbed layers formed from mixtures of proteins", Current Opinion in Colloid & Interface Science 9 (2004), 328-339.

(56) References Cited

OTHER PUBLICATIONS

Bailey et al., "Process technological effects of deletion and amplification of hydrophobins I and II in transformants of *Trichoderma reesi*", Appl. Microbiol. Biotechnol. (2002) 58: 721-727.
Arbuckle, Ice Cream, 2$^{nd}$ Edition, AVI Publishing, 1972, pp. 284 and 285.
Fennema's Food Chemistry, 4$^{th}$ Edition, CRC Press, 2008, pp. 727 and 728.
Dictionary.com, Stabilizer, pp. 1-5, print date Jun. 14, 2010.
Guargum.biz, Guar Gum, pp. 1-2, print date Jun. 14, 2010.
Publication No. JP 61-293348, Dec. 1986—Patent Abstracts of Japan.
Publication No. JP 53006491, Jan. 1978—Patent Abstracts of Japan.
Publication No. JP 03164156, Jul. 1991—Patent Abstracts of Japan.
Co-pending application Cox et al., U.S. Appl. No. 12/578,752, filed Oct. 14, 2009.
Co-pending application Cox et al., U.S. Appl. No. 12/532,670, filed Sep. 23, 2009.
Co-pending application Cox et al., U.S. Appl. No. 12/532,667, filed Sep. 23, 2009.
Co-pending application Cox et al., U.S. Appl. No. 12/780,294, filed May 14, 2010.
Co-pending application Cox et al., U.S. Appl. No. 12/780,323, filed May 14, 2010.
Co-pending application Watts et al., U.S. Appl. No. 12/788,419, filed May 27, 2010.
Co-pending application Bialek et al., U.S. Appl. No. 11/643,586, filed Dec. 21, 2006.

* cited by examiner

Standard sorbet
-abused 2 weeks

Sorbet with Hydrophobin
-abused 2 weeks

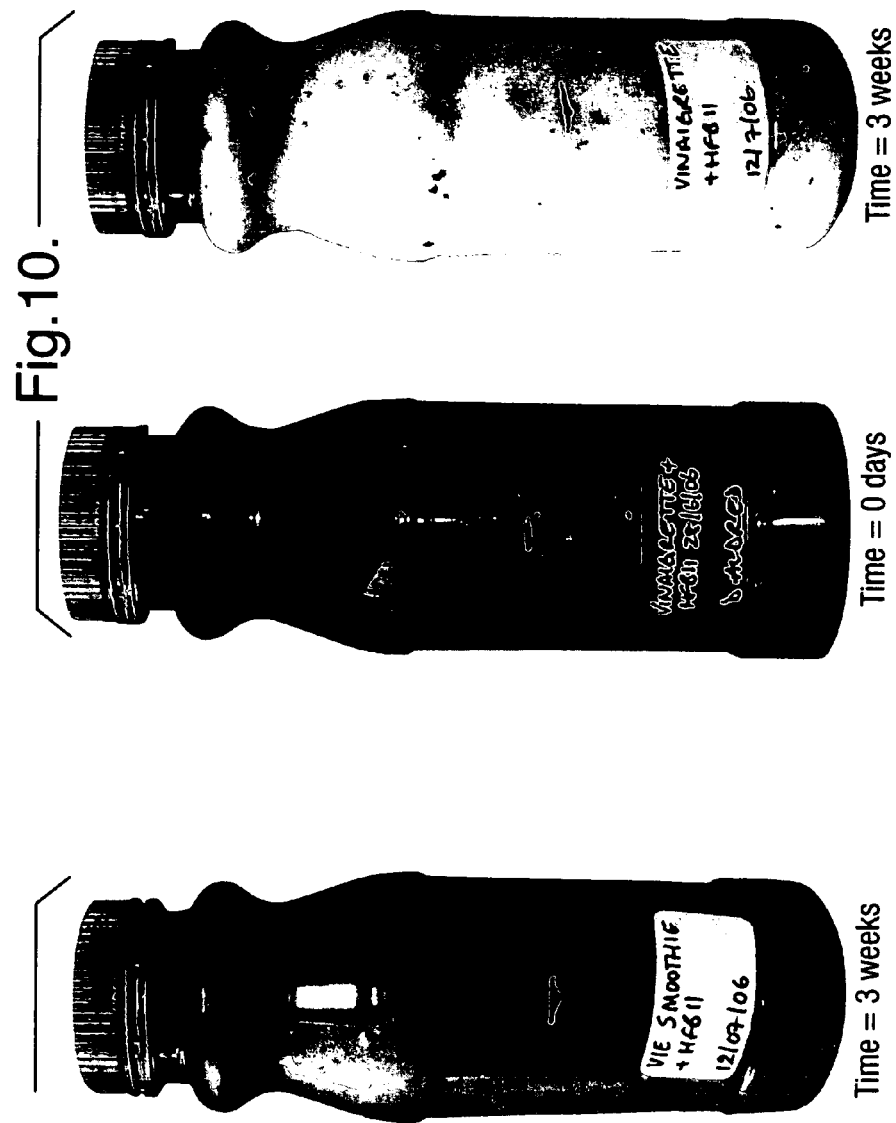

LOW PH AERATED PRODUCTS

FIELD OF THE INVENTION

The present invention relates low pH aerated compositions, such as food products, that include hydrophobins.

BACKGROUND TO THE INVENTION

A wide variety of food products contain introduced gas, such as air, nitrogen and/or carbon dioxide. Typically, aerated food products tend to be of a relatively neutral pH—approximately pH 6.0 to 7.5. Examples of such products include ice cream, whipped toppings and whipped cream.

Most aerated food products comprise proteins and these are essential for both the incorporation of air bubbles and their subsequent stability. However, dairy proteins in particular tend to be pH sensitive. That is, their charge, interactions, and their conformation, can alter as a function of pH. This adversely affects both the foaming ability and the resulting stability of the foams made using protein, particularly for aerated products of pH 5.4 and lower. This is because both the surface activity and the solubility of many proteins are reduced as pH is lowered. For example, sodium caseinate precipitates at about pH 4.6 to 4.8. This results in both poor air incorporation and resulting instability of aerated products.

This fact has been described extensively in the literature and producing stable foams at low pH is a known problem. However, although there are routes described in the art that facilitate the formation of aerated food products at low pH, they tend to have limitations. Such limitations are overcome by the current invention. For example, gelatine is often added as a stabiliser which both thickens the product and also aids in air stability. Most "mousse" products take advantage of the use of gelatine. However, gelatine is an animal based stabiliser which is not seen as a suitable ingredient by many consumers. Furthermore, use of gelatine usually means that the product will be "set", i.e. will not flow. This means one is limited to the type of products that can be made using this formulation technology.

Other methods take advantage of other chemical emulsifier systems such as sucrose esters and/or variants of mono-/diglycerides of saturated fatty acids. Although these non-dairy based formulation technologies will form aeratable products at low pH, often significant quantities of emulsifier are required for long term stability (in excess of 3 weeks). This can have an undesirable influence on both taste and texture. Furthermore, significant quantities of chemical emulsifier in foods are not acceptable to the consumer.

Ideally, a suitable aerating agent would be pH insensitive (in terms of its foaming behaviour), be functional at low concentrations such that no undesirable impact on taste and texture was apparent, and could be used to form aerated foods where the foam was stable in excess of 3 weeks at chill or ambient temperature.

SUMMARY OF THE INVENTION

In our co-pending application, WO 06/010425, we have identified fungal proteins, termed hydrophobins, as being highly effective at stabilising aerated food products. We have now surprisingly found that low concentrations of hydrophobin protein (<0.5 wt. %) can be mixed with acids to form solutions at low pH which are readily foamable and will form foams at chill and ambient temperatures that are stable in excess of 3 weeks. Since hydrophobin does not lead to gelation of the continuous phase or to undesired textures in the mouth, this means that stable foams can be prepared at low pH irrespective of continuous phase rheology. Therefore, the type of aerated product opportunities are wide, for example, aerated acidic smoothies and aerated tea beverages.

These opportunities are not limited to food products but can be applied to other aerated compositions which have a low pH.

Accordingly, the present invention provides an aerated composition having a pH of less than 5.5, which composition comprises hydrophobin.

In one embodiment, the hydrophobin is in a substantially isolated form.

In a preferred embodiment, the hydrophobin is present in an amount of at least 0.001 wt %, more preferably at least 0.01 wt %.

Preferably the hydrophobin is a class II hydrophobin.

The present invention further provides the use of a hydrophobin in a method of inhibiting bubble coarsening in an aerated composition having a pH of less than 5.5.

In a related aspect the present invention provides a method of inhibiting bubble coarsening in an aerated composition having a pH of less than 5.5 which method comprises adding hydrophobin to the composition prior to and/or during aeration of the composition.

The present invention also provides the use of a hydrophobin in a method of stabilising a foam in an aerated composition having a pH of less than 5.5.

In a related aspect the present invention also provides a method of stabilising a foam in an aerated composition having a pH of less than 5.5 which method comprises adding hydrophobin to the composition prior to and/or during aeration of the composition.

DETAILED DESCRIPTION OF THE INVENTION

Unless defined otherwise, all technical and scientific terms used herein have the same meaning as commonly understood by one of ordinary skill in the art (e.g. in chilled confectionery/frozen confectionery manufacture, chemistry and biotechnology). Definitions and descriptions of various terms and techniques used in chilled/frozen confectionery manufacture are found in Ice Cream, 4$^{th}$ Edition, Arbuckle (1986), Van Nostrand Reinhold Company, New York, N.Y. Standard techniques used for molecular and biochemical methods can be found in Sambrook et al., Molecular Cloning: A Laboratory Manual, 3$^{rd}$ ed. (2001) Cold Spring Harbor Laboratory Press, Cold Spring Harbor, N.Y. and Ausubel et al., Short Protocols in Molecular Biology (1999) 4$^{th}$ Ed, John Wiley & Sons, Inc.—and the full version entitled Current Protocols in Molecular Biology).

Hydrophobins

Hydrophobins are a well-defined class of proteins (Wessels, 1997, Adv. Microb. Physio. 38: 1-45; Wosten, 2001, Annu Rev. Microbiol. 55: 625-646) capable of self-assembly at a hydrophobic/hydrophilic interface, and having a conserved sequence:

$$X_n-C-X_{5-9}-C-C-X_{11-39}-C-X_{8-23}-C-$$
$$X_{5-9}-C-C-X_{6-18}-C-X_m \quad \text{(SEQ ID No.1)}$$

where X represents any amino acid, and n and m independently represent an integer. Typically, a hydrophobin has a length of up to 125 amino acids. The cysteine residues (C) in the conserved sequence are part of disulphide bridges. In the context of the present invention, the term hydrophobin has a wider meaning to include functionally equivalent proteins still displaying the characteristic of self-assembly at a hydrophobic-hydrophilic interface resulting in a protein film, such as proteins comprising the sequence:

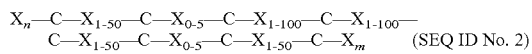

$$X_n\text{—C—}X_{1-50}\text{—C—}X_{0-5}\text{—C—}X_{1-100}\text{—C—}X_{1-100}\text{—}$$
$$\text{C—}X_{1-50}\text{—C—}X_{0-5}\text{—C—}X_{1-50}\text{—C—}X_m \quad \text{(SEQ ID No. 2)}$$

or parts thereof still displaying the characteristic of self-assembly at a hydrophobic-hydrophilic interface resulting in a protein film. In accordance with the definition of the present invention, self-assembly can be detected by adsorbing the protein to Teflon and using Circular Dichroism to establish the presence of a secondary structure (in general, α-helix) (De Vocht et al., 1998, Biophys. J. 74: 2059-68).

The formation of a film can be established by incubating a Teflon sheet in the protein solution followed by at least three washes with water or buffer (Wosten et al., 1994, Embo. J. 13: 5848-54). The protein film can be visualised by any suitable method, such as labeling with a fluorescent marker or by the use of fluorescent antibodies, as is well established in the art. m and n typically have values ranging from 0 to 2000, but more usually m and n in total are less than 100 or 200. The definition of hydrophobin in the context of the present invention includes fusion proteins of a hydrophobin and another polypeptide as well as conjugates of hydrophobin and other molecules such as polysaccharides.

Hydrophobins identified to date are generally classed as either class I or class II. Both types have been identified in fungi as secreted proteins that self-assemble at hydrophobilic interfaces into amphipathic films. Assemblages of class I hydrophobins are relatively insoluble whereas those of class II hydrophobins readily dissolve in a variety of solvents.

Hydrophobin-like proteins have also been identified in filamentous bacteria, such as *Actinomycete* and *Steptomyces* sp. (WO01/74864). These bacterial proteins, by contrast to fungal hydrophobins, form only up to one disulphide bridge since they have only two cysteine residues. Such proteins are an example of functional equivalents to hydrophobins having the consensus sequences shown in SEQ ID Nos. 1 and 2, and are within the scope of the present invention.

The hydrophobins can be obtained by extraction from native sources, such as filamentous fungi, by any suitable process. For example, hydrophobins can be obtained by culturing filamentous fungi that secrete the hydrophobin into the growth medium or by extraction from fungal mycelia with 60% ethanol. It is particularly preferred to isolate hydrophobins from host organisms that naturally secrete hydrophobins. Preferred hosts are *hyphomycetes* (e.g. *Trichoderma*), *basidiomycetes* and *ascomycetes*. Particularly preferred hosts are food grade organisms, such as *Cryphonectria parasitica* which secretes a hydrophobin termed cryparin (MacCabe and Van Alfen, 1999, App. Environ. Microbiol 65: 5431-5435).

Alternatively, hydrophobins can be obtained by the use of recombinant technology. For example host cells, typically micro-organisms, may be modified to express hydrophobins and the hydrophobins can then be isolated and used in accordance with the present invention. Techniques for introducing nucleic acid constructs encoding hydrophobins into host cells are well known in the art. More than 34 genes coding for hydrophobins have been cloned, from over 16 fungal species (see for example WO96/41882 which gives the sequence of hydrophobins identified in *Agaricus bisporus*; and Wosten, 2001, Annu Rev. Microbiol. 55: 625-646). Recombinant technology can also be used to modify hydrophobin sequences or synthesise novel hydrophobins having desired/improved properties.

Typically, an appropriate host cell or organism is transformed by a nucleic acid construct that encodes the desired hydrophobin. The nucleotide sequence coding for the polypeptide can be inserted into a suitable expression vector encoding the necessary elements for transcription and translation and in such a manner that they will be expressed under appropriate conditions (e.g. in proper orientation and correct reading frame and with appropriate targeting and expression sequences). The methods required to construct these expression vectors are well known to those skilled in the art.

A number of expression systems may be used to express the polypeptide coding sequence. These include, but are not limited to, bacteria, fungi (including yeast), insect cell systems, plant cell culture systems and plants all transformed with the appropriate expression vectors. Preferred hosts are those that are considered food grade—'generally regarded as safe' (GRAS).

Suitable fungal species, include yeasts such as (but not limited to) those of the genera *Saccharomyces, Kluyveromyces, Pichia, Hansenula, Candida, Schizo saccharomyces* and the like, and filamentous species such as (but not limited to) those of the genera *Aspergillus, Trichoderma, Mucor, Neurospora, Fusarium* and the like.

The sequences encoding the hydrophobins are preferably at least 80% identical at the amino acid level to a hydrophobin identified in nature, more preferably at least 95% or 100% identical. However, persons skilled in the art may make conservative substitutions or other amino acid changes that do not reduce the biological activity of the hydrophobin. For the purpose of the invention these hydrophobins possessing this high level of identity to a hydrophobin that naturally occurs are also embraced within the term "hydrophobins".

Hydrophobins can be purified from culture media or cellular extracts by, for example, the procedure described in WO01/57076 which involves adsorbing the hydrophobin present in a hydrophobin-containing solution to surface and then contacting the surface with a surfactant, such as Tween 20, to elute the hydrophobin from the surface. See also Collen et al., 2002, Biochim Biophys Acta. 1569: 139-50; Calonje et al., 2002, Can. J. Microbiol. 48: 1030-4; Askolin et al., 2001, Appl Microbiol Biotechnol. 57: 124-30; and De Vries et al., 1999, Eur J Biochem. 262: 377-85.

Aerated Low pH Compositions

By the term "low pH composition", we mean any composition where the pH of the aqueous phase is less than 5.5 for some or all of the product life-time. Preferably the pH is less than 5.4, 5.2 or 5.0. Typically, the pH is equal to or more than 1.0, preferably 3.0 or more, such as 4.0 or more. Typically, for an aerated food, a low pH product would exhibit a pH of from 3.0 to 5.4.

The term "aerated" means that gas has been intentionally incorporated into the product, such as by mechanical means. The gas can be any gas, but is preferably, particularly in the context of food products, a food-grade gas such as air, nitrogen or carbon dioxide. The extent of aeration is typically defined in terms of "overrun". In the context of the present invention, % overrun is defined in volume terms as:

$$((\text{volume of the final aerated product}-\text{volume of the mix})/\text{volume of the mix})\times 100$$

The amount of overrun present in the product will vary depending on the desired product characteristics. For example, the level of overrun in frozen yoghurt is typically from about 70 to 100%, and in confectionery such as mousses the overrun can be as high as 200 to 250 wt %. The level of overrun in some chilled products, ambient products and hot products can be lower, but generally over 10%, e.g. the level of overrun in milkshakes is typically from 10 to 40 wt %.

The level of overrun in other products is preferably from 100 to 800%.

It is not necessary for the foam to be homogeneous within the product. Nonetheless, in one embodiment, the foam is substantially homogeneous.

Aerated compositions of the invention include aerated food products. Other compositions include those where a foam is required within a continuous phase of low pH which can maintain its stability throughout the required time of product use.

Preferably an aerated composition of the invention will retain at least 50% of its original air phase volume, more preferably 75%, for a period of at least 3 weeks (typically measured after storage at chill temperatures (ca. 5° C.)). The overrun does not have to be dispersed homogeneously throughout the product.

Preferably, the average bubble diameter in the composition will not change appreciably over a period of 3 weeks (typically measured after storage at chill temperatures (ca. 5° C.)) from the average size when it was initially prepared at time t=0. Preferably, the relative average bubble diameter ($d_r$) will change less than a factor 2.5 over a period of 3 weeks, and more preferably less than a factor of 2. The relative bubble diameter ($d_r$) at time=t is as determined in the examples through the equation:

$$d_r = \frac{d_t}{d_0}$$

Where $d_0$ is the average diameter immediately after preparation, i.e. t=0, and $d_t$ is the average bubble diameter at time=t.

A suitable method for measuring changes in bubble size and foam volume is by using a light scattering technique. The Turbiscan TLab measurement system (Formulaction, France) can conveniently be used, which analyses both the backscattered and transmitted light from the aerated sample of interest.

The foam to be analysed is contained within a cylindrical sample cell (e.g. with a diameter of 25 mm, filled with 20 ml foam). A light source of wavelength $\lambda$=880 nm is used to supply the incident light, and two optical sensors receive the light transmitted through the sample (180° from the incident light) and back scattered light (45° from the incident light) from the sample. In scanning mode, the optical sensors scan the height of the tube acquiring both transmitted and back-scattered data as a function of sample height and time. Therefore, migration phenomena (such as creaming) and changes in particle size (such as bubble size) can be monitored over time. Relevant theory and examples of the use of the Turbiscan measurement system can be found in: Mengual et al., Colloids and Surfaces A, 1999, 152, 112-123; Rouimi et al., Food Hydrocolloids, 2005, 19, 467-478; Also, application notes and useful information can be obtained from the manufacturer's website: www.turbiscan.com Experimentally, average bubble size changes are best observed by variations in the backscattered light through an area of the sample where other changes (such as foam collapse or bubble creaming) are not occurring. Here, we used central areas of the foam. The backscattering level (BS) is linked to the photon transport mean free path, $\lambda^*$, through the foam by the relation:

$$BS = \frac{1}{(\lambda^*)^{\frac{1}{2}}}$$

$\lambda^*$ is dependent upon the gas volume fraction, $\phi$, and the bubble mean diameter d through:

$$\lambda^* = \frac{2d}{3\phi(1-g)Q}$$

Q and g are both optical parameters from Mie theory, where Q is the scattering efficiency factor and g is an asymmetry factor. For a foam of known volume fraction of air, the change in the average bubble diameter can be monitored over time. This is calculated automatically through the Turbiscan software.

Exact measurement parameters that can be used are stated in the Examples.

Foam stability (volume of foam as a function of time) and extent of creaming can also be determined by a visual method by observing these phenomena in foams sampled into measuring cylinders. Creaming (due to the buoyancy of the air bubbles) is a process which leads to vertical phase separation in the container resulting in a large proportion of bubbles close to the upper surface and the depletion of bubbles at the bottom.

Aerated Food Products

Aerated food products of the invention typically fall into one of four groups—hot, ambient (i.e. products stored and/or served at room temperature without the requirement for refrigeration/freezing), chilled or frozen. The term "food" includes beverages. Chilled aerated food products include smoothies and tea. Frozen aerated food products include frozen confections such as frozen yoghurt.

Suitable acids for use in low pH food products of the invention include, but are not limited to, ascorbic acid, citric acid, lactic acid, tartaric acid, carbonic acid, succinic acid, malic acid, gluconic acid, and mixtures thereof.

Food products may optionally contain other ingredients such as one or more of the following: other proteins such as dairy proteins, either as pure ingredients or as liquid ingredients, e.g. milk or cream; oil or fat, notably in the form of an emulsified phase; sugars; salts; colours and flavours; chemical emulsifiers, such as monoglycerides, tea or coffee; fruit or vegetable purees/extracts/juice; stabilisers or thickeners, such as polysaccharides; preservatives; inclusions, such as nuts, fruit, toffees. Preferably, food products of the invention do not contain gelatine.

Some particular examples of embodiments of the present invention are set out below:

In one embodiment, the product is an aerated beverage such as a milkshake, smoothie, carbonated drink, beer, or tea where a foam is required at low pH and which maintains stability throughout the product life-time. In this case, the overrun of the aerated product may be between 5 and 300%, and most preferably between 10 and 200%. The gas does not need to be-dispersed homogeneously throughout the product.

In a second embodiment, the product is an aerated set food such as a mousse, cheesecake, jam, whipped topping or cream, where a foam is required at low pH and which maintains stability throughout the product life-time. In this case, the preferred overrun is between 50 and 400%.

In a third embodiment, the product is an aerated frozen dessert such as a sorbet, ice cream, or frozen yoghurt, where a foam is required at low pH and which maintains stability throughout the product life-time. The preferred overrun is between 50 and 300%.

Preferably the aerated food product is an aerated confectionery product.

The amount of hydrophobin present in the product will generally vary depending on the product formulation and volume of the air phase. Typically, the product will contain at least 0.001 wt %, hydrophobin, more preferably at least 0.005 or 0.01 wt %. Typically the product will contain less than 1 wt % hydrophobin. The hydrophobin can be from a single source or a plurality of sources e.g. the hydrophobin can a mixture of two or more different hydrophobin polypeptides.

Preferably the hydrophobin is a class II hydrophobin.

The present invention also encompasses compositions for producing an aerated food product of the invention, which composition comprises a hydrophobin. Such compositions include liquid premixes, for example premixes used in the production of frozen confectionery products, and dry mixes, for example powders, to which an aqueous liquid, such as milk or water, is added prior to or during aeration.

The compositions for producing an aerated food product of the invention, will comprise other ingredients, in addition to the hydrophobin, which are normally included in the food product, e.g. sugar, fat, emulsifiers, flavourings etc. The compositions may include all of the remaining ingredients required to make the food product such that the composition is ready to be processed, i.e. aerated, to form an aerated food product of the invention.

Dry compositions for producing an aerated food product of the invention will also comprise other ingredients, in addition to the hydrophobin, which are normally included in the food product, e.g. sugar, fat, emulsifiers, flavourings etc. The compositions may include all of the remaining non-liquid ingredients required to make the food product such that all that the user need only add an aqueous liquid, such as water or milk, and the composition is ready to be processed to form an aerated food product of the invention. These dry compositions, examples of which include powders and granules, can be designed for both industrial and retail use, and benefit from reduced bulk and longer shelf life.

Compositions for producing an aerated food product of the invention will typically have a pH of less than 5.5, or in the case of dry compositions, form a composition having a pH of less than 5.5 when water or milk is added to reconstitute the product to its usual final form.

The hydrophobin is added in a form and in an amount such that it is available to stabilise the air phase. By the term "added", we mean that the hydrophobin is deliberately introduced into the product for the purpose of taking advantage of its foam stabilising properties. Consequently, where ingredients are present or added that contain fungal contaminants, which may contain hydrophobin polypeptides, this does not constitute adding hydrophobin within the context of the present invention.

Typically, the hydrophobin is added to the product in a form such that it is capable of self-assembly at an air-liquid surface.

Typically, the hydrophobin is added to the products or compositions of the invention in an isolated form, typically at least partially purified, such as at least 10% pure, based on weight of solids. By "added in isolated form", we mean that the hydrophobin is not added as part of a naturally-occurring organism, such as a mushroom, which naturally expresses hydrophobins. Instead, the hydrophobin will typically either have been extracted from a naturally-occurring source or obtained by recombinant expression in a host organism.

In one embodiment, the hydrophobin is added to the product in monomeric, dimeric and/or oligomeric (i.e. consisting of 10 monomeric units or fewer) form. Preferably at least 50 wt % of the added hydrophobin is in at least one of these forms, more preferably at least 75, 80, 85 or 90 wt %. Once added, the hydrophobin will typically undergo assembly at the air/liquid interface and therefore the amount of monomer, dimer and oligomer would be expected to decrease.

In one embodiment, the hydrophobin is added to the aerated compositions of the invention in an isolated form, typically at least partially purified.

The added hydrophobin can be used to stabilise the air phase in an aerated composition, generally by inhibiting bubble coarsening, i.e. hydrophobins have been found not only to stabilise foam volume but also the size of the bubbles within the foam.

The present invention will now be described further with reference to the following examples which are illustrative only and non-limiting.

DESCRIPTION OF THE FIGURES

FIG. 9: Photographs of an aerated fruit smoothie product containing 0.1% HFBII and 0.41% xanthan freshly made (left) and after 3 weeks storage at 5° C. (right) showing little creaming or bubble growth.

FIG. 10: Photographs of an aerated vinaigrette product containing 0.1% HFBII and 0.25% xanthan freshly made (left) and after 3 weeks storage at 5° C. (right) showing little creaming or bubble growth.

EXAMPLE 1

Aerated Low pH Products

Figure 1:
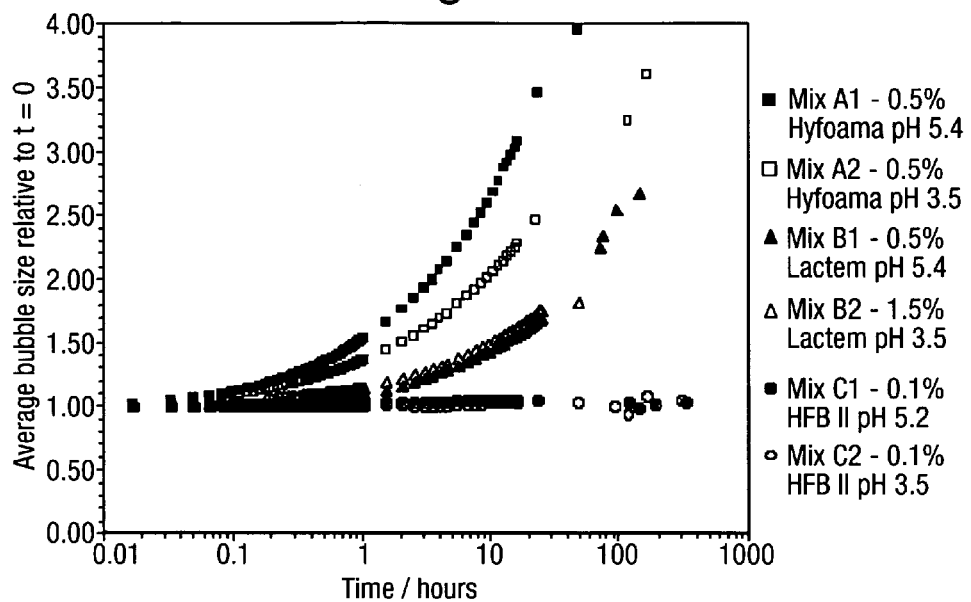
FIG. 1: Average bubble diameter relative to that at time t=0 as a function of time.

Aerated products were prepared comprising solutions containing an acid, xanthan gum, and one of three aerating agents (A-C) listed below.

A: Hyfoama DS

B: Lactic acid ester of monoglyceride (Grinsted Lactem P 22, LACTEM)

C: Hydrophobin (HFBII) from *Trichoderma reesei* (HFBII was obtained from VTT Biotechnology, Finland, purified from *Trichoderma reesei* essentially as described in WO00/58342 and Linder et al., 2001, Biomacromolecules 2: 511-517).

Details of the materials used are summarised in Table 1 and the formulations from which each of the foam samples was prepared are shown in Table 2 (Mixes A to C).

Xanthan was added to each mix in order to prevent creaming of the foam. This allows full analysis of bubble size as a function of time without the complication of other destabilising factors such as creaming. In other words, we are measuring the stability of the foams to destabilising mechanisms such as disproportionation and coalescence.

Mix Preparation

For Mix A the protein and xanthan gum were blended and added slowly into agitated water at room temperature. The solutions were subsequently heated to 40° C. to ensure that proteins were properly dissolved, with a total mixing time of 30 minutes. The mixes were cooled and stored at 5° C. until further use.

For Mix B the Lactem and xanthan were dispersed into agitated water at room temperature. This dispersion was then heated to 60° C. to ensure that the Lactem is properly dispersed, with a total mixing time of 30 minutes. The mixes were cooled and stored at 5° C. until further use.

For Mix C the xanthan was added slowly to cold water with agitation and stirred for at least 30 minutes to ensure that the polymer was fully hydrated. Then, the required concentration of HFB II was added as an aliquot. The solution was then gently sonicated in a sonic bath for 30 seconds to fully dissolve the HFB II. The mix was cooled and stored at 5° C. until further use.

TABLE 1

Materials used

| Ingredient | Composition | Supplier |
|---|---|---|
| Hyfoama DS | 65% protein | Quest |
| Grinsted Lactem P22 (Lactic acid ester) | 100% fat (Lactic acid content 20-25%) | Danisco |
| Hydrophobin HFB II | Purified from *T. reesei* | VTT Biotechnology, Finland. |
| Xanthan Gum (Keltrol RD) | polysaccharide | CP Kelco |

TABLE 2

Base Formulations used before addition of acid.

| Ingredient | Mix A | Mix B | Mix C |
|---|---|---|---|
| | Concentration/wt % | | |
| Hyfoama DS | 0.5 | — | — |
| Lactem | — | 1.5 | — |
| HFB II | — | — | 0.1 |
| Xanthan gum | 0.5 | 0.5 | 0.5 |
| Water | 99.0 | 98.0 | 99.4 |

Aerating Process

Before aeration the sample solutions were acidified to the desired pH of either 5.4 or 3.5 using a 10 wt % solution of citric acid. These are summarised in Table 3.

TABLE 3 pH of mixes after addition of citric acid.

| Mix/Aerated Product | pH |
|---|---|
| A1 (from Mix A) | 5.4 |
| A2 (from Mix A) | 3.5 |
| B1 (from Mix B) | 5.4 |
| B2 (from Mix B) | 3.5 |
| C1 (from Mix C) | 5.2 |
| C2 (from Mix C) | 3.5 |

80 mL of the acidified mix was sheared using a stirred pot apparatus for a timed duration that corresponded to obtaining 100% overrun. This equipment consists of a cylindrical, vertically mounted, jacketed stainless steel vessel with internal proportions of 105 mm height and diameter 72 mm.

The rotor used to shear the sample consists of a rectangular impeller of the correct proportions to scrape the inner surface of the vessel as it rotates (dimensions 72 mm×41.5 mm). Also attached to the rotor are two semi-circular (60 mm diameter) high-shear blades positioned at a 45° angle to the rectangular attachment. The rate was 1200 rpm and the steel vessel containing the rotor was cooled to 5° C. during aeration.

Post aeration, samples were stored at 5° C. in Turbiscan vials or 100 mL measuring cylinders before further analysis.

Measurement of Foam and Bubble Stability

The stability of the foam and the bubbles therein was measured using the Turbiscan TLab, the operating details of which are discussed above. This enables the determination of the following as a function of time: (1) The foam volume (i.e. measurement of overall air phase loss). (2) The average bubble size.

The produced foam was dosed into a Turbiscan glass sample tube up to a height of about 42 mm, corresponding to approximately 20 mL of foam. The equipment then scans and measures both the backscattered and transmitted light between the height of 2 and 55 mm. Measurements were taken over a period of several weeks, depending on the stability of the foam. Since data is collected over the full sample height, from this, the mean values of the backscattering profiles between defined limits (lower and upper height) give specific information with respect to changes in the sample in that area, e.g. bubble size.

Bubble size: From the backscattered data measured between 20 and 30 mm, the average bubble size was calculated automatically from the backscattered light. The refractive indices were taken as those of water and air. The air phase volume fraction of the foam was 0.5 (equating to 100% overrun). Although the air phase volume fraction of the foam can change over time, particularly if it is not stable and creaming takes place, we found that taking measurements between 20 and 30 mm height of the sample gave reliable size data unless the foam was very unstable. If the foam was highly unstable, then the size data needs to be treated with caution in a quantitative sense but can be compared with that of other foams.

Results and Discussion

Stability as a Function of Time

The average bubble size (relative to that measured at t=0 min) measured for each of the foamed mixes as a function of time is shown in FIG. 1. At both pH 3.5 and 5.2, HFBII forms a foam where the bubbles remain stable far in excess of those in the foams aerated using either Hyfoama or Lactem. The foam stabilised by HFBII remained stable for in excess of 3 weeks.

As well as significant bubble growth, the foams created using Hyfoama and Lactem collapsed (lost air phase volume)

in the later stages of their short life-time. In the case of HFBII, no measured air phase volume was lost from the product.

Figure 2:
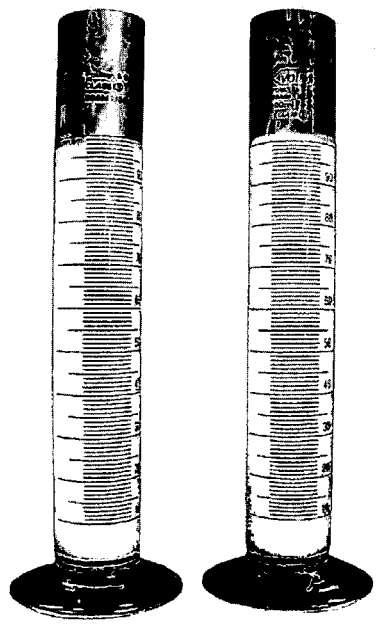
FIG. 2: Foams created using 0.1% HFBII and 0.5% xanthan at pH 3.5 and 5.2 (left and right, respectively) and stored at 5° C. for 3 weeks. After this period of time, no loss of foam volume or bubble visible bubble growth has occurred.
Figure 3:
FIG. 3: Foams created at pH 3.5 containing 0.5% xanthan and (left) 0.1% HFBII—3 weeks storage, (centre) 1.5% LACTEM—2 weeks storage, and (right) 0.5% hyfoama—3 weeks storage. All stored at 5° C.

FIGS. 2 and 3 show images of foams created using HFBII, Lactem, or Hyfoama as the aerating agent. FIG. 2 clearly demonstrates that the foam created using HFBII is highly stable at both pH 3.5 and 5.4. Even after 3 weeks storage, no foam collapse or visible bubble growth could be observed.

Figure 4:
FIG. 4: Close up picture of foams created at pH 3.5 containing 0.5% xanthan and (left) 0.1% HFBII—3 weeks storage, (right) 1.5% LACTEM—2 weeks storage. Note that the example with HFBII shows a foam where bubbles are not visible whereas the foam with LACTEM shows visible bubbles that have grown during storage.
Figure 4:

FIGS. 3 and 4 again demonstrate the stability of the foam created using HFBII. The foam made using Lactem at pH 3.4 shows reasonable stability in terms of retaining the air phase volume, but it is clear that significant bubble growth has occurred, as can be seen from the close up picture in FIG. 4 showing visible air bubbles. In the case of Hyfoama, significant bubble growth has occurred, but also air phase volume has been lost.

Therefore, it is clear that hydrophobin can be used to form highly stable foams in the presence of acids. These foams retain their air phase volume over a period of 3 weeks at chill, and the bubble size does not change significantly during that time.

EXAMPLE 2

Aerated Product Containing Tea Extract

Preparation of Aerated Product

A mix containing tea extract of the following formulation was made. 0.1% HFBII, 0.5% xanthan, 0.16% green tea powder, and the remainder water. The mix was prepared as follows: The xanthan and green tea powder were slowly add to cold water with agitation and stirred for at least 30 minutes to ensure that the polymer was fully hydrated. Then, the required concentration of HFB II was added as an aliquot. The solution was then gently sonicated in a sonic bath for 30 seconds to fully dissolve the HFB II. The mix was cooled and stored at 5° C. until further use.

Before aeration the solution was acidified to the desired pH of 5.4 using a 10 wt % solution of citric acid. The mix was then aerated to 100% overrun using the stirred pot in the same manner as described for the mixes in Example 1. The aerated mix was then stored at 5° C. and analysis of bubble size and foam volume was made as a function of time using the Turbiscan with the same experimental set up as described in Example 1.

Results and Discussion

Figure 5:
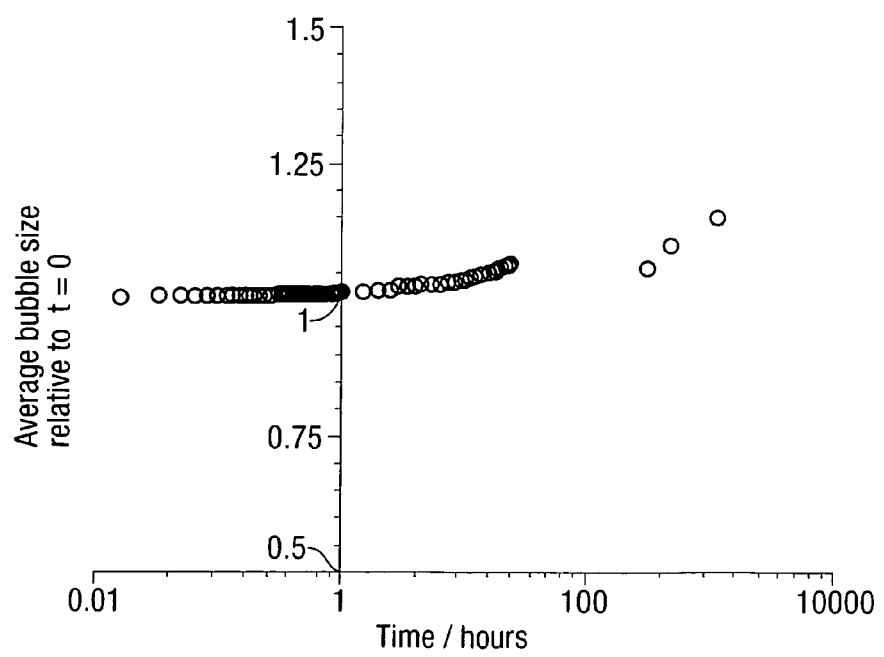
FIG. 5: Average bubble diameter relative to that at time t=0 as a function of time for green tea containing foam.

The stability of the foam in terms of average bubble diameter is shown in FIG. 5. Clearly, over a period of time there is minimal change in bubble size indicating that the bubbles are stable to significant change. Furthermore, the overall foam volume remained constant over this time period.

EXAMPLE 3

Aerated and Frozen Fruit Sorbet

Two sorbets were produced using the ingredients listed in Table 4. Product J was produced using the formulation for Mix J, described in Table 5. The air stabilising agent in this product was a commercially available aerating agent called Hygel, a hydrolysed milk protein. Product K was produced using the formulation shown for Mix K. The air stabilising protein in this product was hydrophobin, HFBII.

TABLE 4

| Materials used | |
| --- | --- |
| Ingredient | Details and Supplier |
| Sucrose | Tate and Lyle |
| LF9 | 63DE corn syrup, C*Trusweet 017Y4, Cerestar, UK |
| Xanthan gum (Keltrol RD) | CPKelco |
| Citric acid | Jungbunzlauer AG |
| Strawberry puree | SVZ International BV |
| Hydrophobin HFB II | Purified from *Trichoderma reesei*, purchased from VTT Biotechnology, Finland |
| Hygel 8293 | A hydrolysed milk protein, minimum 80% protein, obtained from Kerry Bioscience, UK. |

TABLE 5

| | Formulations | |
| --- | --- | --- |
| | Mix J | Mix K |
| Ingredient | Concentration/wt % | |
| HFB II | 0 | 0.1 |
| Hygel | 0.2 | 0 |
| Xanthan gum | 0.2 | 0.2 |
| Citric acid | 0.2 | 0.2 |
| Sucrose | 10.5 | 10.5 |
| LF9 | 17.3 | 17.3 |
| Strawberry puree | 20.0 | 20.0 |
| Water | 51.6 | 51.7 |

Mix Preparation

For Mix J all the ingredients were added to cold water, dispersed using a magnetic stirrer and heated to 80° C. with continuous mixing. The solution was cooled rapidly to 5° C. using a cooling bath set at −18° C. For Mix K, comprising hydrophobin, the same procedure was followed except that the HFB II was added to the cooled solution as an aliquot. The mixes were stored at 5° C. before further processing. The pH of the unaerated mix was measured to be pH 4.

Aeration and Freezing Step 80 mL of cold mix was transferred into the stirred pot (described in Example 1) for aeration and freezing. Freezing was achieved by circulating coolant through the jacket surrounding the stirred pot. The mix was aerated and frozen to produce a sorbet product using the following shear and temperature regime: 100 rpm for 1 minute, switch on coolant circulation (at −18° C.), then 1000 rpm for 2 minutes, then 300 rpm until the torque reached 1 Nm (this occurred at a product temperature of −5° C.). The sorbets were collected into suitable containers which had been cooled to below −20° C. The overrun of Product J was measured to be 113% and the overrun of Product K was 101%.

Storage and Temperature Abuse Regimes

The sorbet products were subsequently stored under two temperature regimes:
  (a) "Fresh" samples were stored at −80° C. for until they were analysed (about 1 week). At −80° C. no structural changes occur, so that the microstructure is essentially the same as for a fresh sample.
  (b) "Temperature abused" samples were stored at −10° C. for 1 week. Some samples were also stored for a further week at −10° C.

After storage, the products were analysed by Scanning Electron Microscopy (SEM) as well as by visual inspection of the overall product quality.

Scanning Electron Microscopy

The microstructure of the products was visualised using low temperature Scanning Electron Microscopy (SEM). To prepare specimens for microscopy, the sample was cooled to −80° C. on dry ice and a section was cut. This section, approximately 6 mm×6 mm×10 mm in size, was mounted on a sample holder using a Tissue Tek: OCT™ compound (PVA 11%, Carbowax 5% and 85% non-reactive components) on the point of freezing. The sample including the holder was plunged into liquid nitrogen slush and transferred to a low temperature preparation chamber (Oxford Instrument CT1500HF) held under vacuum, approximately $10^{-4}$ mbar. The sample was fractured inside the chamber using a scalpel blade. The sample was then warmed up to −90° C. for approximately 60 to 90 seconds so that ice slowly sublimed to reveal surface details. It was then cooled to −110° C. to end the sublimation. The sample was next coated with gold using argon plasma. This process also took place under vacuum with an applied pressure of $10^{-1}$ mbar and current of 6 milliamps for 45 seconds. The sample was then transferred to a conventional Scanning Electron Microscope (JSM 5600), fitted with an Oxford Instruments cold stage at a temperature of −150° C. The sample was imaged and areas of interest were captured via digital image acquisition software.

Results

Figure 6:
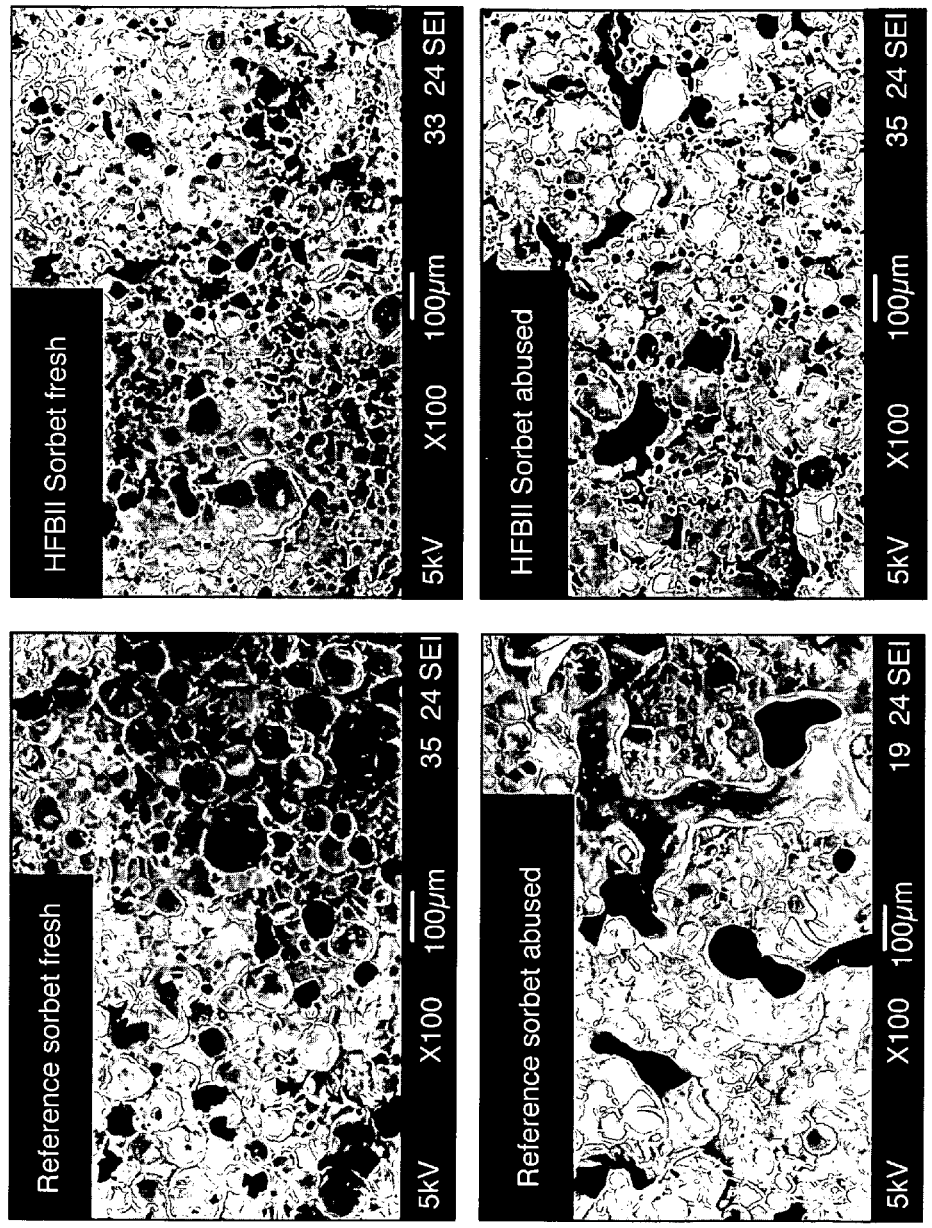
FIG. 6: SEM images of the microstructure of sorbets created using 0.2% hygel and 0.1% HFBII, both fresh and after temperature abuse.

FIG. 6 shows SEM images of the microstructures of: (left) product J, the comparative product; and (right) product K, according to the invention. The upper images show the fresh products and the lower ones show the temperature abused products.

The fresh products have similar microstructures with small, spherical air bubbles. However, after temperature abuse the comparative product J shows large air channels and very few discrete air cells, indicating that severe bubble coalescence has taken place. Product K according to the invention (i.e. containing hydrophobin) shows much less coalescence and channelling of the air phase and retains a large number of small discrete bubbles.

Figure 7:
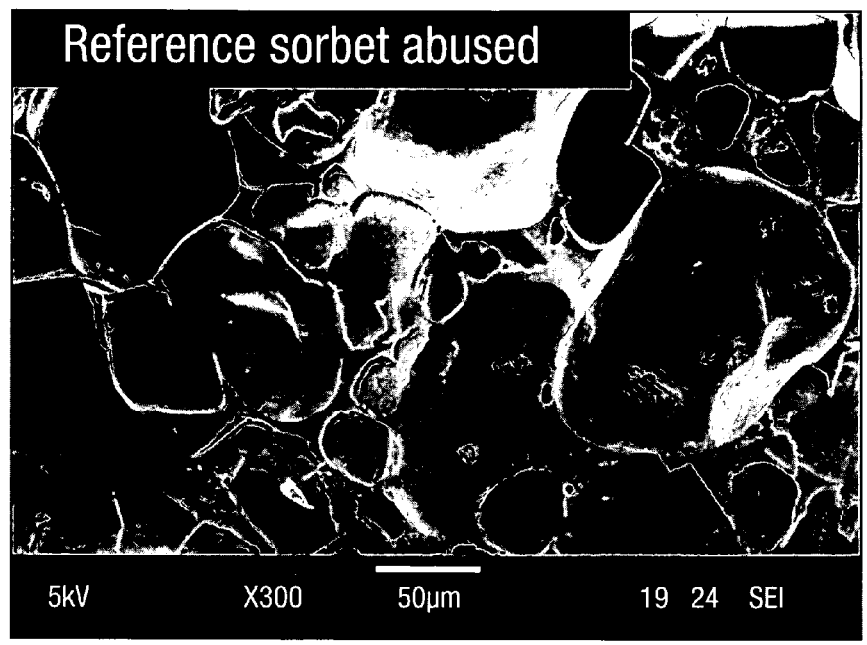
FIG. 7: Higher magnification SEM images of the microstructure of sorbets created using 0.2% hygel and 0.1% HFBII, after temperature abuse.
Figure 7:
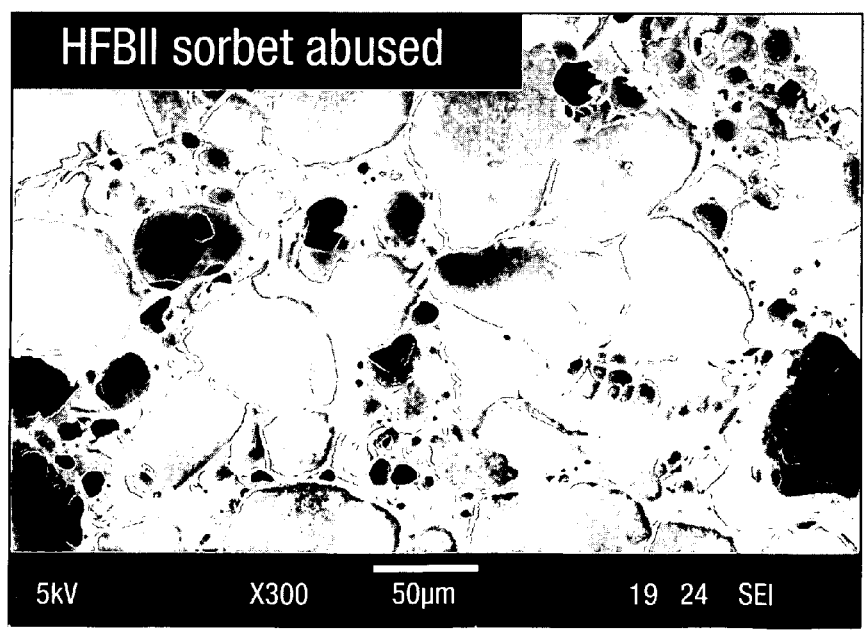

FIG. 7 shows the microstructure of the temperature abused samples at a higher magnification. Sorbet K shows the presence of small air bubbles (less than 100 μm in diameter) where as Sorbet J does not.

Figure 8:
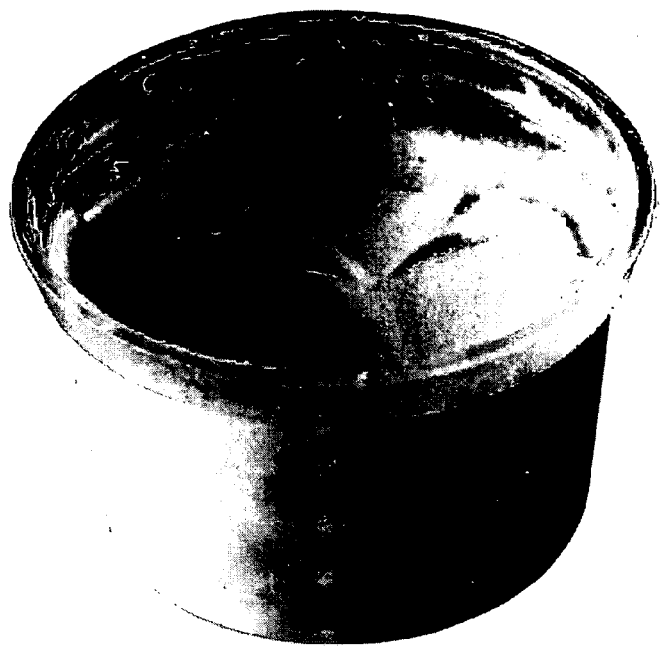
FIG. 8: Photographs of sorbets created using 0.2% hygel and 0.1% HFBII after 2 weeks temperature abuse.
Figure 8:
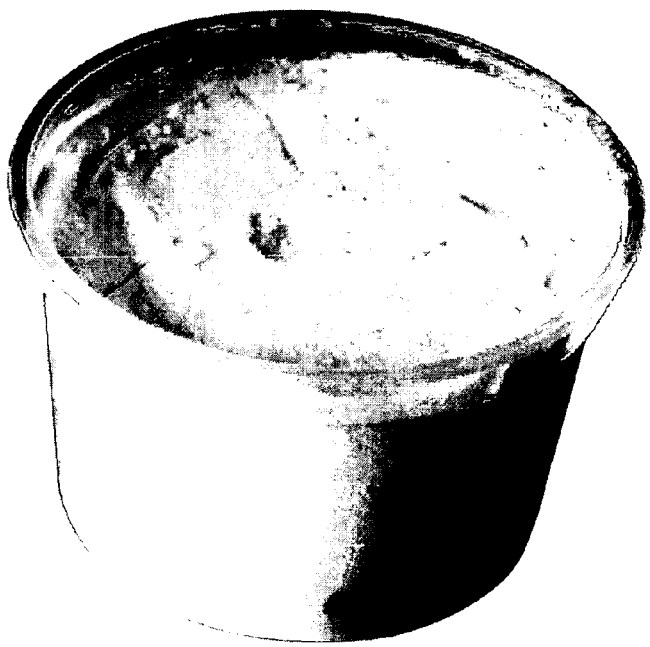

FIG. 8 shows a photograph of the comparative sorbet product (J) and the sorbet product comprising hydrophobin (K) after temperature abuse for 2 weeks. Sorbet J is darker than sorbet K due to the increase in bubble size in the sample. Furthermore, Sorbet J has decreased in volume due to loss of air, where as Sorbet K has not.

From these images it is evident that a low pH sorbet containing hydrophobin (K) has a substantially more stable air phase than a comparative sorbet (J) containing a standard air stabilising milk protein.

EXAMPLE 4

Aerated Fruit Smoothie

An aerated fruit smoothie was prepared using a Vie Shots™ drink, produced by Unilever UK as a fruit puree base. The Vie Shot™ contained: banana puree (28%), orange juice concentrate (26%), carrot juice concentrate (23%), pumpkin juice concentrate (14%), orange pulp (4%), lemon juice concentrate, acerola cherry concentrate (1.5%), and apple pectin. The pH was measured (at room temperature) to be pH 4.17. Xanthan gum was slowly added to the fruit puree with stirring, to a concentration of 0.5 wt. %. This was then mixed for 20 minutes to allow the xanthan gum to hydrate fully. A known volume of 0.5 wt. % hydrophobin solution was aerated to 400% overrun using a hand held Aerolatte™ device. This was added to the fruit puree to give an aerated fruit smoothie product with approximately 100% overrun, an overall hydrophobin concentration of 0.1 wt % and an overall xanthan concentration of about 0.41 wt %. The aerated fruit smoothie product was then stored at 5° C. and its stability monitored over a period of three weeks. FIG. 9 shows that after 3 weeks the aerated fruit smoothie product retained a stable air phase and that no significant bubble growth or creaming occurred.

EXAMPLE 5

Vinaigrette Dressing

An aerated dressing was prepared using Hellman's™ Light Vinaigrette as a base. The base contained: water, spirit vinegar, sugar, modified potato starch, garlic, salt, red pepper, preservative, parsley, black pepper, thyme and colour. The pH was measured (at room temperature) to be pH 3.58. Xanthan gum was slowly added to the vinaigrette with stirring, to a concentration of 0.3 wt. %. It was then mixed for 20 minutes to allow the xanthan gum to hydrate fully. A known volume of 0.5 wt. % hydrophobin solution was aerated to 400% overrun using a hand held Aerolatte™ device. This was added to the vinaigrette dressing to give an aerated vinaigrette dressing product with approximately 100% overrun, an overall hydrophobin concentration of 0.1 wt % and an overall xanthan concentration of about 0.25 wt %. The product was then stored at 5° C. and the stability monitored over a period of three weeks. FIG. 10 shows that after 3 weeks there was no significant foam collapse or bubble growth. There was also no significant amount of creaming. Therefore, hydrophobin is able to adequately stabilise a foam in a pourable low pH dressing for at least 3 weeks.

The various features and embodiments of the present invention, referred to in individual sections above apply, as appropriate, to other sections, mutatis mutandis. Consequently features specified in one section may be combined with features specified in other sections, as appropriate.

All publications mentioned in the above specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the following claims.

The invention claimed is:

1. An aerated composition, said aerated composition having a pH of less than 5.5, and an overrun of between 10 and 800%, which composition comprises at least 0.001 wt % class II hydrophobin wherein the hydrophobin is added in an isolated form, wherein the relative average bubble diameter, dr will change less than a factor of 2.0 over a period of 3 weeks after storage at ca.5° C.

2. An aerated food product according to claim 1 which is a chilled food product.

3. An aerated composition according to claim 1 having a pH of from 3.0 to 5.4.

4. An aerated composition according to claim 1 having a pH of from 3.0 to 5.0.

5. The aerated composition according to claim 1 further comprising an acid selected from the group of ascorbic add, lactic acid, tartaric add, carbonic acid, citric add, succinic acid, malic acid, gluconic acid, vinegar, and mixtures thereof.

6. An aerated composition containing tea or coffee, said aerated composition having a pH of less than 5.5 and an overrun of between 10 and 800%, which composition comprises at least 0.001 wt % class II hydrophobin added in an isolated form, wherein the relative average bubble diameter, $d_r$ will change less than a factor of 2.0 over a period of 3 weeks after storage at ca.5° C.

7. An aerated composition containing tea or coffee, said aerated composition having a pH of less than 5.5 and an overrun of between 10 and 800%, which composition comprises at least 0.001 wt % class II hydrophobin obtained by use of recombinant technology, wherein the relative average bubble diameter, $d_r$ will change less than a factor of 2.0 over a period of 3 weeks after storage at ca.5'C.

8. The aerated composition according to claim 6 wherein the hydrophobin is a form which is at least partially purified such that it is at least 10% pure based on weight of solids.

9. The aerated composition according to claim 1 wherein the hydrophobin comprises HFBII.

10. The aerated composition according to claim 6 wherein the hydrophobin comprises HFBII.

11. An aerated composition selected from the group of smoothies, sorbets, and frozen yogurt, comprising an ingredient selected from the group of fruit puree, fruit extract, fruit juice and fruit inclusions, said aerated composition having a pH of less than 5.5 and an overrun of between 10 and 800%, which composition comprises at least 0.001 wt % class II hydrophobin added in an isolated form, wherein the relative average bubble diameter, $d_r$ will change less than a factor of 2.0 over a period of 3 weeks after storage at ca.5° C.

12. The aerated composition according to claim 11 wherein the hydrophobin comprises HFBII.

13. An aerated dressing composition, said aerated dressing composition having a pH of less than 5.5 and an overrun of between 10 and 800%, which composition comprises at least 0.001 wt % class II hydrophobin wherein the hydrophobin is obtained by use of recombinant technology, wherein the relative average bubble diameter, $d_r$ will change less than a factor of 2.0 over a period of 3 weeks after storage at ca.5° C.

14. An aerated dressing composition, said aerated dressing composition having a pH of less than 5.5 and an overrun of between 10 and 800%, which composition comprises at least 0.001 wt % class II hydrophobin added in an isolated form, wherein the relative average bubble diameter, $d_r$ will change less than a factor of 2.0 over a period of 3 weeks after storage at ca.5° C.

15. An aerated composition selected from the group of smoothies, sorbets, frozen yogurt, beverages and dressings comprising an ingredient selected from the group of ascorbic acid, citric acid, lactic add, tartaric acid, carbonic acid, succinic acid, malic acid, and vinegar having a pH of less than 5.5 and an overrun of between 10 and 800%, which composition comprises at least 0.001 wt % class II hydrophobin wherein the hydrophobin is added in an isolated form, wherein the relative average bubble diameter, $d_r$ will change less than a factor of 2.0 over a period of 3 weeks after storage at ca.5° C.

16. The aerated composition according to claim 15 wherein the hydrophobin is obtained by use of recombinant technology.

17. The aerated composition according to claim 1, wherein the hydrophobin is obtained by use of recombinant technology.

18. The flowable aerated food composition according to claim 1 wherein the hydrophobin is in a form which is at least partially purified such that it is at least 10% pure based on weight of solids.

19. The flowable aerated food composition according to claim 11 wherein the hydrophobin is obtained by use of recombinant technology.

20. The food composition according to claim 1 wherein the hydrophobin is added to the product in a form such that it is capable of self-assembly at an air-liquid surface.

21. The food composition according to claim 17 wherein the hydrophobin is obtained by modifying host cells to express hydrophobin.

22. The food composition according to claim 1 comprising less than 1 wt % hydrophobin.

* * * * *

UNITED STATES PATENT AND TRADEMARK OFFICE
CERTIFICATE OF CORRECTION

PATENT NO. : 8,993,030 B2  
APPLICATION NO. : 11/525060  
DATED : March 31, 2015  
INVENTOR(S) : Deborah Lynne Aldred et al.

Page 1 of 1

It is certified that error appears in the above-identified patent and that said Letters Patent is hereby corrected as shown below:

On the Title Page

Item (56), Other Publications:
"Atomic Resolution Structire" should be "Atomic Resolution Structure"
"a Self-assenbling" should be "a Self-assembling"

In the Claims

Column 57, line 30, Claim 1:
"bubble diameter, dr" should be "bubble diameter, $d_r$"

Column 57, line 57, Claim 7:
"5'C" should be "5°C"

Signed and Sealed this
Twenty-first Day of July, 2015

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 4106
<212> TYPE: PRT
```

```
<213> ORGANISM: Artificial
<220> FEATURE:
<223> OTHER INFORMATION: Exemplary sequence used to illustrate invention.
<220> FEATURE:
<221> NAME/KEY: REPEAT
<222> LOCATION: (1)..(2000)
<223> OTHER INFORMATION: Xaa is any amino acid and can be shown 1 to
      2000 times.
<220> FEATURE:
<221> NAME/KEY: REPEAT
<222> LOCATION: (2002)..(2010)
<223> OTHER INFORMATION: Xaa is any amino acid and can be shown 5 to
      9 times.
<220> FEATURE:
<221> NAME/KEY: REPEAT
<222> LOCATION: (2013)..(2051)
<223> OTHER INFORMATION: Xaa is any amino acid and can be shown 11 to
      39 times.
<220> FEATURE:
<221> NAME/KEY: REPEAT
<222> LOCATION: (2053)..(2075)
<223> OTHER INFORMATION: Xaa is any amino acid and can be shown 8 to 23
      times.
<220> FEATURE:
<221> NAME/KEY: REPEAT
<222> LOCATION: (2077)..(2085)
<223> OTHER INFORMATION: Xaa is any amino acid and can be shown 5 to 9
      times.
<220> FEATURE:
<221> NAME/KEY: REPEAT
<222> LOCATION: (2088)..(2105)
<223> OTHER INFORMATION: Xaa is any amino acid and can be shown 6 to 18
      times.
<220> FEATURE:
<221> NAME/KEY: REPEAT
<222> LOCATION: (2107)..(4106)
<223> OTHER INFORMATION: indefinite repeats.  Xaa is any amino acid.

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205
```

-continued

Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa Xaa Xaa
    275                 280                 285

Xaa Xaa Xaa Xaa Xaa Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
        340                 345                 350

Xaa Xaa Xaa Xaa Xaa Xaa Xaa Xaa Xaa Xaa Xaa Xaa Xaa Xaa Xaa
    355                 360                 365

Xaa Xaa Xaa Xaa Xaa Xaa Xaa Xaa Xaa Xaa Xaa Xaa Xaa Xaa Xaa
370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa
    435                 440                 445

Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Xaa Xaa Xaa Xaa Xaa Xaa Xaa Xaa Xaa
    515                 520                 525

Xaa Xaa Xaa Xaa Xaa Xaa Xaa Xaa Xaa Xaa Xaa Xaa Xaa Xaa Xaa
530                 535                 540

Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa
        580                 585                 590

Xaa Xaa Xaa Xaa Xaa Xaa Xaa Xaa Xaa Xaa Xaa Xaa Xaa Xaa Xaa
    595                 600                 605

Xaa Xaa Xaa Xaa Xaa Xaa Xaa Xaa Xaa Xaa Xaa Xaa Xaa Xaa Xaa
610                 615                 620

Xaa Xaa Xaa Xaa Xaa Xaa Xaa Xaa Xaa Xaa Xaa Xaa Xaa Xaa Xaa

```
              625                 630                 635                 640

Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa Xaa Xaa
            690                 695                 700

Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
            725                 730                 735

Xaa Xaa Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa Xaa Xaa
            755                 760                 765

Xaa Xaa Xaa Xaa Xaa Xaa Xaa Xaa Xaa Xaa Xaa Xaa Xaa Xaa Xaa
            770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Xaa Xaa Xaa Xaa Xaa Xaa Xaa
            835                 840                 845

Xaa Xaa Xaa Xaa Xaa Xaa Xaa Xaa Xaa Xaa Xaa Xaa Xaa Xaa Xaa
            850                 855                 860

Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa
            885                 890                 895

Xaa Xaa Xaa Xaa Xaa Xaa Xaa Xaa Xaa Xaa Xaa Xaa Xaa Xaa Xaa
            900                 905                 910

Xaa Xaa Xaa Xaa Xaa Xaa Xaa Xaa Xaa Xaa Xaa Xaa Xaa Xaa Xaa
            915                 920                 925

Xaa Xaa Xaa Xaa Xaa Xaa Xaa Xaa Xaa Xaa Xaa Xaa Xaa Xaa Xaa
            930                 935                 940

Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Xaa Xaa Xaa Xaa
            965                 970                 975

Xaa Xaa Xaa Xaa Xaa Xaa Xaa Xaa Xaa Xaa Xaa Xaa Xaa Xaa Xaa
            980                 985                 990

Xaa Xaa Xaa Xaa Xaa Xaa Xaa Xaa Xaa Xaa Xaa Xaa Xaa Xaa Xaa
            995                1000                1005

Xaa Xaa Xaa Xaa Xaa Xaa Xaa Xaa Xaa Xaa Xaa Xaa Xaa Xaa Xaa
           1010                1015                1020

Xaa Xaa Xaa Xaa Xaa Xaa Xaa Xaa Xaa Xaa Xaa Xaa Xaa Xaa Xaa
1025                1030                1035                1040

Xaa Xaa Xaa Xaa Xaa Xaa Xaa Xaa Xaa Xaa Xaa Xaa Xaa Xaa Xaa
           1045                1050                1055
```

-continued

Xaa Xaa Xaa Xaa Xaa Xaa Xaa Xaa Xaa Xaa Xaa Xaa Xaa Xaa Xaa
            1060                1065                1070

Xaa Xaa Xaa Xaa Xaa Xaa Xaa Xaa Xaa Xaa Xaa Xaa Xaa Xaa Xaa
        1075                1080                1085

Xaa Xaa Xaa Xaa Xaa Xaa Xaa Xaa Xaa Xaa Xaa Xaa Xaa Xaa Xaa
            1090                1095                1100

Xaa Xaa Xaa Xaa Xaa Xaa Xaa Xaa Xaa Xaa Xaa Xaa Xaa Xaa Xaa
1105                1110                1115                1120

Xaa Xaa Xaa Xaa Xaa Xaa Xaa Xaa Xaa Xaa Xaa Xaa Xaa Xaa Xaa
            1125                1130                1135

Xaa Xaa Xaa Xaa Xaa Xaa Xaa Xaa Xaa Xaa Xaa Xaa Xaa Xaa Xaa
        1140                1145                1150

Xaa Xaa Xaa Xaa Xaa Xaa Xaa Xaa Xaa Xaa Xaa Xaa Xaa Xaa Xaa
            1155                1160                1165

Xaa Xaa Xaa Xaa Xaa Xaa Xaa Xaa Xaa Xaa Xaa Xaa Xaa Xaa Xaa
        1170                1175                1180

Xaa Xaa Xaa Xaa Xaa Xaa Xaa Xaa Xaa Xaa Xaa Xaa Xaa Xaa Xaa
1185                1190                1195                1200

Xaa Xaa Xaa Xaa Xaa Xaa Xaa Xaa Xaa Xaa Xaa Xaa Xaa Xaa Xaa
            1205                1210                1215

Xaa Xaa Xaa Xaa Xaa Xaa Xaa Xaa Xaa Xaa Xaa Xaa Xaa Xaa Xaa
            1220                1225                1230

Xaa Xaa Xaa Xaa Xaa Xaa Xaa Xaa Xaa Xaa Xaa Xaa Xaa Xaa Xaa
        1235                1240                1245

Xaa Xaa Xaa Xaa Xaa Xaa Xaa Xaa Xaa Xaa Xaa Xaa Xaa Xaa Xaa
            1250                1255                1260

Xaa Xaa Xaa Xaa Xaa Xaa Xaa Xaa Xaa Xaa Xaa Xaa Xaa Xaa Xaa
1265                1270                1275                1280

Xaa Xaa Xaa Xaa Xaa Xaa Xaa Xaa Xaa Xaa Xaa Xaa Xaa Xaa Xaa
            1285                1290                1295

Xaa Xaa Xaa Xaa Xaa Xaa Xaa Xaa Xaa Xaa Xaa Xaa Xaa Xaa Xaa
        1300                1305                1310

Xaa Xaa Xaa Xaa Xaa Xaa Xaa Xaa Xaa Xaa Xaa Xaa Xaa Xaa Xaa
        1315                1320                1325

Xaa Xaa Xaa Xaa Xaa Xaa Xaa Xaa Xaa Xaa Xaa Xaa Xaa Xaa Xaa
        1330                1335                1340

Xaa Xaa Xaa Xaa Xaa Xaa Xaa Xaa Xaa Xaa Xaa Xaa Xaa Xaa Xaa
1345                1350                1355                1360

Xaa Xaa Xaa Xaa Xaa Xaa Xaa Xaa Xaa Xaa Xaa Xaa Xaa Xaa Xaa
            1365                1370                1375

Xaa Xaa Xaa Xaa Xaa Xaa Xaa Xaa Xaa Xaa Xaa Xaa Xaa Xaa Xaa
            1380                1385                1390

Xaa Xaa Xaa Xaa Xaa Xaa Xaa Xaa Xaa Xaa Xaa Xaa Xaa Xaa Xaa
        1395                1400                1405

Xaa Xaa Xaa Xaa Xaa Xaa Xaa Xaa Xaa Xaa Xaa Xaa Xaa Xaa Xaa
    1410                1415                1420

Xaa Xaa Xaa Xaa Xaa Xaa Xaa Xaa Xaa Xaa Xaa Xaa Xaa Xaa Xaa
1425                1430                1435                1440

Xaa Xaa Xaa Xaa Xaa Xaa Xaa Xaa Xaa Xaa Xaa Xaa Xaa Xaa Xaa
            1445                1450                1455

Xaa Xaa Xaa Xaa Xaa Xaa Xaa Xaa Xaa Xaa Xaa Xaa Xaa Xaa Xaa
            1460                1465                1470

```
Xaa Xaa Xaa Xaa Xaa Xaa Xaa Xaa Xaa Xaa Xaa Xaa Xaa Xaa Xaa
        1475                1480                1485

Xaa Xaa Xaa Xaa Xaa Xaa Xaa Xaa Xaa Xaa Xaa Xaa Xaa Xaa Xaa
        1490                1495                1500

Xaa Xaa Xaa Xaa Xaa Xaa Xaa Xaa Xaa Xaa Xaa Xaa Xaa Xaa Xaa
1505                1510                1515                1520

Xaa Xaa Xaa Xaa Xaa Xaa Xaa Xaa Xaa Xaa Xaa Xaa Xaa Xaa Xaa
        1525                1530                1535

Xaa Xaa Xaa Xaa Xaa Xaa Xaa Xaa Xaa Xaa Xaa Xaa Xaa Xaa Xaa
        1540                1545                1550

Xaa Xaa Xaa Xaa Xaa Xaa Xaa Xaa Xaa Xaa Xaa Xaa Xaa Xaa Xaa
        1555                1560                1565

Xaa Xaa Xaa Xaa Xaa Xaa Xaa Xaa Xaa Xaa Xaa Xaa Xaa Xaa Xaa
        1570                1575                1580

Xaa Xaa Xaa Xaa Xaa Xaa Xaa Xaa Xaa Xaa Xaa Xaa Xaa Xaa Xaa
1585                1590                1595                1600

Xaa Xaa Xaa Xaa Xaa Xaa Xaa Xaa Xaa Xaa Xaa Xaa Xaa Xaa Xaa
        1605                1610                1615

Xaa Xaa Xaa Xaa Xaa Xaa Xaa Xaa Xaa Xaa Xaa Xaa Xaa Xaa Xaa
        1620                1625                1630

Xaa Xaa Xaa Xaa Xaa Xaa Xaa Xaa Xaa Xaa Xaa Xaa Xaa Xaa Xaa
        1635                1640                1645

Xaa Xaa Xaa Xaa Xaa Xaa Xaa Xaa Xaa Xaa Xaa Xaa Xaa Xaa Xaa
        1650                1655                1660

Xaa Xaa Xaa Xaa Xaa Xaa Xaa Xaa Xaa Xaa Xaa Xaa Xaa Xaa Xaa
1665                1670                1675                1680

Xaa Xaa Xaa Xaa Xaa Xaa Xaa Xaa Xaa Xaa Xaa Xaa Xaa Xaa Xaa
        1685                1690                1695

Xaa Xaa Xaa Xaa Xaa Xaa Xaa Xaa Xaa Xaa Xaa Xaa Xaa Xaa Xaa
        1700                1705                1710

Xaa Xaa Xaa Xaa Xaa Xaa Xaa Xaa Xaa Xaa Xaa Xaa Xaa Xaa Xaa
        1715                1720                1725

Xaa Xaa Xaa Xaa Xaa Xaa Xaa Xaa Xaa Xaa Xaa Xaa Xaa Xaa Xaa
        1730                1735                1740

Xaa Xaa Xaa Xaa Xaa Xaa Xaa Xaa Xaa Xaa Xaa Xaa Xaa Xaa Xaa
1745                1750                1755                1760

Xaa Xaa Xaa Xaa Xaa Xaa Xaa Xaa Xaa Xaa Xaa Xaa Xaa Xaa Xaa
        1765                1770                1775

Xaa Xaa Xaa Xaa Xaa Xaa Xaa Xaa Xaa Xaa Xaa Xaa Xaa Xaa Xaa
        1780                1785                1790

Xaa Xaa Xaa Xaa Xaa Xaa Xaa Xaa Xaa Xaa Xaa Xaa Xaa Xaa Xaa
        1795                1800                1805

Xaa Xaa Xaa Xaa Xaa Xaa Xaa Xaa Xaa Xaa Xaa Xaa Xaa Xaa Xaa
        1810                1815                1820

Xaa Xaa Xaa Xaa Xaa Xaa Xaa Xaa Xaa Xaa Xaa Xaa Xaa Xaa Xaa
1825                1830                1835                1840

Xaa Xaa Xaa Xaa Xaa Xaa Xaa Xaa Xaa Xaa Xaa Xaa Xaa Xaa Xaa
        1845                1850                1855

Xaa Xaa Xaa Xaa Xaa Xaa Xaa Xaa Xaa Xaa Xaa Xaa Xaa Xaa Xaa
        1860                1865                1870

Xaa Xaa Xaa Xaa Xaa Xaa Xaa Xaa Xaa Xaa Xaa Xaa Xaa Xaa Xaa
        1875                1880                1885

Xaa Xaa Xaa Xaa Xaa Xaa Xaa Xaa Xaa Xaa Xaa Xaa Xaa Xaa Xaa
```

-continued

```
                        1890                1895                1900

Xaa Xaa Xaa Xaa Xaa Xaa Xaa Xaa Xaa Xaa Xaa Xaa Xaa Xaa Xaa Xaa
1905                1910                1915                1920

Xaa Xaa Xaa Xaa Xaa Xaa Xaa Xaa Xaa Xaa Xaa Xaa Xaa Xaa Xaa
        1925                1930                1935

Xaa Xaa Xaa Xaa Xaa Xaa Xaa Xaa Xaa Xaa Xaa Xaa Xaa Xaa Xaa
        1940                1945                1950

Xaa Xaa Xaa Xaa Xaa Xaa Xaa Xaa Xaa Xaa Xaa Xaa Xaa Xaa Xaa
        1955                1960                1965

Xaa Xaa Xaa Xaa Xaa Xaa Xaa Xaa Xaa Xaa Xaa Xaa Xaa Xaa Xaa
        1970                1975                1980

Xaa Xaa Xaa Xaa Xaa Xaa Xaa Xaa Xaa Xaa Xaa Xaa Xaa Xaa Xaa Xaa
1985                1990                1995                2000

Cys Xaa Xaa Xaa Xaa Xaa Xaa Xaa Xaa Cys Cys Xaa Xaa Xaa Xaa
        2005                2010                2015

Xaa Xaa Xaa Xaa Xaa Xaa Xaa Xaa

-continued

Xaa Xaa Xaa Xaa Xaa Xaa Xaa Xaa Xaa Xaa Xaa Xaa Xaa Xaa Xaa
         2325                2330                2335

Xaa Xaa Xaa Xaa Xaa Xaa Xaa Xaa Xaa Xaa Xaa Xaa Xaa Xaa Xaa
         2340                2345                2350

Xaa Xaa Xaa Xaa Xaa Xaa Xaa Xaa Xaa Xaa Xaa Xaa Xaa Xaa Xaa
         2355                2360                2365

Xaa Xaa Xaa Xaa Xaa Xaa Xaa Xaa Xaa Xaa Xaa Xaa Xaa Xaa Xaa
         2370                2375                2380

Xaa Xaa Xaa Xaa Xaa Xaa Xaa Xaa Xaa Xaa Xaa Xaa Xaa Xaa Xaa
2385              2390                2395                2400

Xaa Xaa Xaa Xaa Xaa Xaa Xaa Xaa Xaa Xaa Xaa Xaa Xaa Xaa Xaa
         2405                2410                2415

Xaa Xaa Xaa Xaa Xaa Xaa Xaa Xaa Xaa Xaa Xaa Xaa Xaa Xaa Xaa
         2420                2425                2430

Xaa Xaa Xaa Xaa Xaa Xaa Xaa Xaa Xaa Xaa Xaa Xaa Xaa Xaa Xaa
         2435                2440                2445

Xaa Xaa Xaa Xaa Xaa Xaa Xaa Xaa Xaa Xaa Xaa Xaa Xaa Xaa Xaa
         2450                2455                2460

Xaa Xaa Xaa Xaa Xaa Xaa Xaa Xaa Xaa Xaa Xaa Xaa Xaa Xaa Xaa
2465              2470                2475                2480

Xaa Xaa Xaa Xaa Xaa Xaa Xaa Xaa Xaa Xaa Xaa Xaa Xaa Xaa Xaa
         2485                2490                2495

Xaa Xaa Xaa Xaa Xaa Xaa Xaa Xaa Xaa Xaa Xaa Xaa Xaa Xaa Xaa
         2500                2505                2510

Xaa Xaa Xaa Xaa Xaa Xaa Xaa Xaa Xaa Xaa Xaa Xaa Xaa Xaa Xaa
         2515                2520                2525

Xaa Xaa Xaa Xaa Xaa Xaa Xaa Xaa Xaa Xaa Xaa Xaa Xaa Xaa Xaa
         2530                2535                2540

Xaa Xaa Xaa Xaa Xaa Xaa Xaa Xaa Xaa Xaa Xaa Xaa Xaa Xaa Xaa
2545              2550                2555                2560

Xaa Xaa Xaa Xaa Xaa Xaa Xaa Xaa Xaa Xaa Xaa Xaa Xaa Xaa Xaa
         2565                2570                2575

Xaa Xaa Xaa Xaa Xaa Xaa Xaa Xaa Xaa Xaa Xaa Xaa Xaa Xaa Xaa
         2580                2585                2590

Xaa Xaa Xaa Xaa Xaa Xaa Xaa Xaa Xaa Xaa Xaa Xaa Xaa Xaa Xaa
         2595                2600                2605

Xaa Xaa Xaa Xaa Xaa Xaa Xaa Xaa Xaa Xaa Xaa Xaa Xaa Xaa Xaa
         2610                2615                2620

Xaa Xaa Xaa Xaa Xaa Xaa Xaa Xaa Xaa Xaa Xaa Xaa Xaa Xaa Xaa
2625              2630                2635                2640

Xaa Xaa Xaa Xaa Xaa Xaa Xaa Xaa Xaa Xaa Xaa Xaa Xaa Xaa Xaa
         2645                2650                2655

Xaa Xaa Xaa Xaa Xaa Xaa Xaa Xaa Xaa Xaa Xaa Xaa Xaa Xaa Xaa
         2660                2665                2670

Xaa Xaa Xaa Xaa Xaa Xaa Xaa Xaa Xaa Xaa Xaa Xaa Xaa Xaa Xaa
         2675                2680                2685

Xaa Xaa Xaa Xaa Xaa Xaa Xaa Xaa Xaa Xaa Xaa Xaa Xaa Xaa Xaa
         2690                2695                2700

Xaa Xaa Xaa Xaa Xaa Xaa Xaa Xaa Xaa Xaa Xaa Xaa Xaa Xaa Xaa
2705              2710                2715                2720

Xaa Xaa Xaa Xaa Xaa Xaa Xaa Xaa Xaa Xaa Xaa Xaa Xaa Xaa Xaa
         2725                2730                2735

-continued

Xaa Xaa Xaa Xaa Xaa Xaa Xaa Xaa Xaa Xaa Xaa Xaa Xaa Xaa Xaa
        2740                2745                2750

Xaa Xaa Xaa Xaa Xaa Xaa Xaa Xaa Xaa Xaa Xaa Xaa Xaa Xaa Xaa
        2755                2760                2765

Xaa Xaa Xaa Xaa Xaa Xaa Xaa Xaa Xaa Xaa Xaa Xaa Xaa Xaa Xaa
        2770                2775                2780

Xaa Xaa Xaa Xaa Xaa Xaa Xaa Xaa Xaa Xaa Xaa Xaa Xaa Xaa Xaa
2785            2790                2795                2800

Xaa Xaa Xaa Xaa Xaa Xaa Xaa Xaa Xaa Xaa Xaa Xaa Xaa Xaa Xaa
        2805                2810                2815

Xaa Xaa Xaa Xaa Xaa Xaa Xaa Xaa Xaa Xaa Xaa Xaa Xaa Xaa Xaa
        2820                2825                2830

Xaa Xaa Xaa Xaa Xaa Xaa Xaa Xaa Xaa Xaa Xaa Xaa Xaa Xaa Xaa
        2835                2840                2845

Xaa Xaa Xaa Xaa Xaa Xaa Xaa Xaa Xaa Xaa Xaa Xaa Xaa Xaa Xaa
        2850                2855                2860

Xaa Xaa Xaa Xaa Xaa Xaa Xaa Xaa Xaa Xaa Xaa Xaa Xaa Xaa Xaa
2865            2870                2875                2880

Xaa Xaa Xaa Xaa Xaa Xaa Xaa Xaa Xaa Xaa Xaa Xaa Xaa Xaa Xaa
        2885                2890                2895

Xaa Xaa Xaa Xaa Xaa Xaa Xaa Xaa Xaa Xaa Xaa Xaa Xaa Xaa Xaa
        2900                2905                2910

Xaa Xaa Xaa Xaa Xaa Xaa Xaa Xaa Xaa Xaa Xaa Xaa Xaa Xaa Xaa
        2915                2920                2925

Xaa Xaa Xaa Xaa Xaa Xaa Xaa Xaa Xaa Xaa Xaa Xaa Xaa Xaa Xaa
        2930                2935                2940

Xaa Xaa Xaa Xaa Xaa Xaa Xaa Xaa Xaa Xaa Xaa Xaa Xaa Xaa Xaa
2945            2950                2955                2960

Xaa Xaa Xaa Xaa Xaa Xaa Xaa Xaa Xaa Xaa Xaa Xaa Xaa Xaa Xaa
        2965                2970                2975

Xaa Xaa Xaa Xaa Xaa Xaa Xaa Xaa Xaa Xaa Xaa Xaa Xaa Xaa Xaa
        2980                2985                2990

Xaa Xaa Xaa Xaa Xaa Xaa Xaa Xaa Xaa Xaa Xaa Xaa Xaa Xaa Xaa
        2995                3000                3005

Xaa Xaa Xaa Xaa Xaa Xaa Xaa Xaa Xaa Xaa Xaa Xaa Xaa Xaa Xaa
        3010                3015                3020

Xaa Xaa Xaa Xaa Xaa Xaa Xaa Xaa Xaa Xaa Xaa Xaa Xaa Xaa Xaa
3025            3030                3035                3040

Xaa Xaa Xaa Xaa Xaa Xaa Xaa Xaa Xaa Xaa Xaa Xaa Xaa Xaa Xaa
        3045                3050                3055

Xaa Xaa Xaa Xaa Xaa Xaa Xaa Xaa Xaa Xaa Xaa Xaa Xaa Xaa Xaa
        3060                3065                3070

Xaa Xaa Xaa Xaa Xaa Xaa Xaa Xaa Xaa Xaa Xaa Xaa Xaa Xaa Xaa
        3075                3080                3085

Xaa Xaa Xaa Xaa Xaa Xaa Xaa Xaa Xaa Xaa Xaa Xaa Xaa Xaa Xaa
        3090                3095                3100

Xaa Xaa Xaa Xaa Xaa Xaa Xaa Xaa Xaa Xaa Xaa Xaa Xaa Xaa Xaa
3105            3110                3115                3120

Xaa Xaa Xaa Xaa Xaa Xaa Xaa Xaa Xaa Xaa Xaa Xaa Xaa Xaa Xaa
        3125                3130                3135

Xaa Xaa Xaa Xaa Xaa Xaa Xaa Xaa Xaa Xaa Xaa Xaa Xaa Xaa Xaa
        3140                3145                3150

Xaa Xaa Xaa Xaa Xaa Xaa Xaa Xaa Xaa Xaa Xaa Xaa Xaa Xaa Xaa

-continued

```
                    3155            3160            3165

Xaa Xaa Xaa Xaa Xaa Xaa Xaa Xaa Xaa Xaa Xaa Xaa Xaa Xaa Xaa
    3170            3175            3180

Xaa Xaa Xaa Xaa Xaa Xaa Xaa Xaa Xaa Xaa Xaa Xaa Xaa Xaa Xaa
3185            3190            3195            3200

Xaa Xaa Xaa Xaa Xaa Xaa Xaa Xaa Xaa Xaa Xaa Xaa Xaa Xaa Xaa
            3205            3210            3215

Xaa Xaa Xaa Xaa Xaa Xaa Xaa Xaa Xaa Xaa Xaa Xaa Xaa Xaa Xaa
        3220            3225            3230

Xaa Xaa Xaa Xaa Xaa Xaa Xaa Xaa Xaa Xaa Xaa Xaa Xaa Xaa Xaa
            3235            3240            3245

Xaa Xaa Xaa Xaa Xaa Xaa Xaa Xaa Xaa Xaa Xaa Xaa Xaa Xaa Xaa
        3250            3255            3260

Xaa Xaa Xaa Xaa Xaa Xaa Xaa Xaa Xaa Xaa Xaa Xaa Xaa Xaa Xaa
3265            3270            3275            3280

Xaa Xaa Xaa Xaa Xaa Xaa Xaa Xaa Xaa Xaa Xaa Xaa Xaa Xaa Xaa
            3285            3290            3295

Xaa Xaa Xaa Xaa Xaa Xaa Xaa Xaa Xaa Xaa Xaa Xaa Xaa Xaa Xaa
        3300            3305            3310

Xaa Xaa Xaa Xaa Xaa Xaa Xaa Xaa Xaa Xaa Xaa Xaa Xaa Xaa Xaa
    3315            3320            3325

Xaa Xaa Xaa Xaa Xaa Xaa Xaa Xaa Xaa Xaa Xaa Xaa Xaa Xaa Xaa
3330            3335            3340

Xaa Xaa Xaa Xaa Xaa Xaa Xaa Xaa Xaa Xaa Xaa Xaa Xaa Xaa Xaa
3345            3350            3355            3360

Xaa Xaa Xaa Xaa Xaa Xaa Xaa Xaa Xaa Xaa Xaa Xaa Xaa Xaa Xaa
        3365            3370            3375

Xaa Xaa Xaa Xaa Xaa Xaa Xaa Xaa Xaa Xaa Xaa Xaa Xaa Xaa Xaa
            3380            3385            3390

Xaa Xaa Xaa Xaa Xaa Xaa Xaa Xaa Xaa Xaa Xaa Xaa Xaa Xaa Xaa
    3395            3400            3405

Xaa Xaa Xaa Xaa Xaa Xaa Xaa Xaa Xaa Xaa Xaa Xaa Xaa Xaa Xaa
3410            3415            3420

Xaa Xaa Xaa Xaa Xaa Xaa Xaa Xaa Xaa Xaa Xaa Xaa Xaa Xaa Xaa
3425            3430            3435            3440

Xaa Xaa Xaa Xaa Xaa Xaa Xaa Xaa Xaa Xaa Xaa Xaa Xaa Xaa Xaa
            3445            3450            3455

Xaa Xaa Xaa Xaa Xaa Xaa Xaa Xaa Xaa Xaa Xaa Xaa Xaa Xaa Xaa
        3460            3465            3470

Xaa Xaa Xaa Xaa Xaa Xaa Xaa Xaa Xaa Xaa Xaa Xaa Xaa Xaa Xaa
    3475            3480            3485

Xaa Xaa Xaa Xaa Xaa Xaa Xaa Xaa Xaa Xaa Xaa Xaa Xaa Xaa Xaa
        3490            3495            3500

Xaa Xaa Xaa Xaa Xaa Xaa Xaa Xaa Xaa Xaa Xaa Xaa Xaa Xaa Xaa
3505            3510            3515            3520

Xaa Xaa Xaa Xaa Xaa Xaa Xaa Xaa Xaa Xaa Xaa Xaa Xaa Xaa Xaa
            3525            3530            3535

Xaa Xaa Xaa Xaa Xaa Xaa Xaa Xaa Xaa Xaa Xaa Xaa Xaa Xaa Xaa
        3540            3545            3550

Xaa Xaa Xaa Xaa Xaa Xaa Xaa Xaa Xaa Xaa Xaa Xaa Xaa Xaa Xaa
    3555            3560            3565

Xaa Xaa Xaa Xaa Xaa Xaa Xaa Xaa Xaa Xaa Xaa Xaa Xaa Xaa Xaa
    3570            3575            3580
```

-continued

Xaa Xaa Xaa Xaa Xaa Xaa Xaa Xaa Xaa Xaa Xaa Xaa Xaa Xaa Xaa Xaa
3585                3590                3595                3600

Xaa Xaa Xaa Xaa Xaa Xaa Xaa Xaa Xaa Xaa Xaa Xaa Xaa Xaa Xaa
        3605                3610                3615

Xaa Xaa Xaa Xaa Xaa Xaa Xaa Xaa Xaa Xaa Xaa Xaa Xaa Xaa Xaa
    3620                3625                3630

Xaa Xaa Xaa Xaa Xaa Xaa Xaa Xaa Xaa Xaa Xaa Xaa Xaa Xaa Xaa
        3635                3640                3645

Xaa Xaa Xaa Xaa Xaa Xaa Xaa Xaa Xaa Xaa Xaa Xaa Xaa Xaa Xaa
    3650                3655                3660

Xaa Xaa Xaa Xaa Xaa Xaa Xaa Xaa Xaa Xaa Xaa Xaa Xaa Xaa Xaa Xaa
3665                3670                3675                3680

Xaa Xaa Xaa Xaa Xaa Xaa Xaa Xaa Xaa Xaa Xaa Xaa Xaa Xaa Xaa
        3685                3690                3695

Xaa Xaa Xaa Xaa Xaa Xaa Xaa Xaa Xaa Xaa Xaa Xaa Xaa Xaa Xaa
    3700                3705                3710

Xaa Xaa Xaa Xaa Xaa Xaa Xaa Xaa Xaa Xaa Xaa Xaa Xaa Xaa Xaa
        3715                3720                3725

Xaa Xaa Xaa Xaa Xaa Xaa Xaa Xaa Xaa Xaa Xaa Xaa Xaa Xaa Xaa
    3730                3735                3740

Xaa Xaa Xaa Xaa Xaa Xaa Xaa Xaa Xaa Xaa Xaa Xaa Xaa Xaa Xaa Xaa
3745                3750                3755                3760

Xaa Xaa Xaa Xaa Xaa Xaa Xaa Xaa Xaa Xaa Xaa Xaa Xaa Xaa Xaa
        3765                3770                3775

Xaa Xaa Xaa Xaa Xaa Xaa Xaa Xaa Xaa Xaa Xaa Xaa Xaa Xaa Xaa
    3780                3785                3790

Xaa Xaa Xaa Xaa Xaa Xaa Xaa Xaa Xaa Xaa Xaa Xaa Xaa Xaa Xaa
        3795                3800                3805

Xaa Xaa Xaa Xaa Xaa Xaa Xaa Xaa Xaa Xaa Xaa Xaa Xaa Xaa Xaa
    3810                3815                3820

Xaa Xaa Xaa Xaa Xaa Xaa Xaa Xaa Xaa Xaa Xaa Xaa Xaa Xaa Xaa Xaa
3825                3830                3835                3840

Xaa Xaa Xaa Xaa Xaa Xaa Xaa Xaa Xaa Xaa Xaa Xaa Xaa Xaa Xaa
        3845                3850                3855

Xaa Xaa Xaa Xaa Xaa Xaa Xaa Xaa Xaa Xaa Xaa Xaa Xaa Xaa Xaa
    3860                3865                3870

Xaa Xaa Xaa Xaa Xaa Xaa Xaa Xaa Xaa Xaa Xaa Xaa Xaa Xaa Xaa
        3875                3880                3885

Xaa Xaa Xaa Xaa Xaa Xaa Xaa Xaa Xaa Xaa Xaa Xaa Xaa Xaa Xaa
    3890                3895                3900

Xaa Xaa Xaa Xaa Xaa Xaa Xaa Xaa Xaa Xaa Xaa Xaa Xaa Xaa Xaa Xaa
3905                3910                3915                3920

Xaa Xaa Xaa Xaa Xaa Xaa Xaa Xaa Xaa Xaa Xaa Xaa Xaa Xaa Xaa
        3925                3930                3935

Xaa Xaa Xaa Xaa Xaa Xaa Xaa Xaa Xaa Xaa Xaa Xaa Xaa Xaa Xaa
    3940                3945                3950

Xaa Xaa Xaa Xaa Xaa Xaa Xaa Xaa Xaa Xaa Xaa Xaa Xaa Xaa Xaa
        3955                3960                3965

Xaa Xaa Xaa Xaa Xaa Xaa Xaa Xaa Xaa Xaa Xaa Xaa Xaa Xaa Xaa
    3970                3975                3980

Xaa Xaa Xaa Xaa Xaa Xaa Xaa Xaa Xaa Xaa Xaa Xaa Xaa Xaa Xaa Xaa
3985                3990                3995                4000

-continued

```
Xaa Xaa Xaa Xaa Xaa Xaa Xaa Xaa Xaa Xaa Xaa Xaa Xaa
                4005            4010            4015

Xaa Xaa Xaa Xaa Xaa Xaa Xaa Xaa Xaa Xaa Xaa Xaa Xaa
            4020            4025            4030

Xaa Xaa Xaa Xaa Xaa Xaa Xaa Xaa Xaa Xaa Xaa Xaa Xaa
        4035            4040            4045

Xaa Xaa Xaa Xaa Xaa Xaa Xaa Xaa Xaa Xaa Xaa Xaa Xaa
    4050            4055            4060

Xaa Xaa Xaa Xaa Xaa Xaa Xaa Xaa Xaa Xaa Xaa Xaa Xaa
4065            4070            4075            4080

Xaa Xaa Xaa Xaa Xaa Xaa Xaa Xaa Xaa Xaa Xaa Xaa Xaa
                4085            4090            4095

Xaa Xaa Xaa Xaa Xaa Xaa Xaa Xaa Xaa Xaa
            4100            4105

<210> SEQ ID NO 2
<211> LENGTH: 4368
<212> TYPE: PRT
<213> ORGANISM: Artificial
<220> FEATURE:
<223> OTHER INFORMATION: Exemplary sequence used to illustrate invention.
<220> FEATURE:
<221> NAME/KEY: REPEAT
<222> LOCATION: (1)..(2000)
<223> OTHER INFORMATION: Xaa is any amino acid and can be shown 1 to
      2000 times.
<220> FEATURE:
<221> NAME/KEY: REPEAT
<222> LOCATION: (2002)..(2051)
<223> OTHER INFORMATION: Xaa is any amino acid and can be shown 1 to 50
      times.
<220> FEATURE:
<221> NAME/KEY: REPEAT
<222> LOCATION: (2053)..(2057)
<223> OTHER INFORMATION: Xaa is any amino acid and can be shown 0 to 5
      times.
<220> FEATURE:
<221> NAME/KEY: REPEAT
<222> LOCATION: (2059)..(2158)
<223> OTHER INFORMATION: Xaa is any amino acid and can be shown 1 to 100
      times.
<220> FEATURE:
<221> NAME/KEY: REPEAT
<222> LOCATION: (2160)..(2259)
<223> OTHER INFORMATION: Xaa is any amino acid and can be shown 1 to 100
      times.
<220> FEATURE:
<221> NAME/KEY: REPEAT
<222> LOCATION: (2261)..(2310)
<223> OTHER INFORMATION: Xaa is any amino acid and can be shown 1 to 50
      times.
<220> FEATURE:
<221> NAME/KEY: REPEAT
<222> LOCATION: (2312)..(2316)
<223> OTHER INFORMATION: Xaa is any amino acid and can be shown 0 to 5
      times.
<220> FEATURE:
<221> NAME/KEY: REPEAT
<222> LOCATION: (2318)..(2367)
<223> OTHER INFORMATION: Xaa is any amino acid and can be shown 1 to 50
      times.
<220> FEATURE:
<221> NAME/KEY: REPEAT
<222> LOCATION: (2369)..(4368)
<223> OTHER INFORMATION: Xaa is any amino acid and can be shown 1 to
      2000 times.

<400> SEQUENCE: 2

Xaa Xaa Xaa Xaa Xaa Xaa Xaa Xaa Xaa Xaa Xaa Xaa Xaa Xaa Xaa Xaa
1               5                   10                  15
```

-continued

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa

-continued

```
                435                 440                 445
Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa
            515                 520                 525

Xaa Xaa Xaa Xaa Xaa Xaa Xaa Xaa Xaa Xaa Xaa Xaa Xaa Xaa Xaa
            530                 535                 540

Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa
        675                 680                 685

Xaa Xaa Xaa Xaa Xaa Xaa Xaa Xaa Xaa Xaa Xaa Xaa Xaa Xaa Xaa
    690                 695                 700

Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
                725                 730                 735

Xaa Xaa Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa Xaa Xaa
        755                 760                 765

Xaa Xaa Xaa Xaa Xaa Xaa Xaa Xaa Xaa Xaa Xaa Xaa Xaa Xaa Xaa
    770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa
                805                 810                 815

Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Xaa Xaa Xaa Xaa Xaa Xaa Xaa
        835                 840                 845

Xaa Xaa Xaa Xaa Xaa Xaa Xaa Xaa Xaa Xaa Xaa Xaa Xaa Xaa Xaa
    850                 855                 860
```

-continued

Xaa Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa
            885                 890                 895

Xaa Xaa Xaa Xaa Xaa Xaa Xaa Xaa Xaa Xaa Xaa Xaa Xaa Xaa Xaa
            900                 905                 910

Xaa Xaa Xaa Xaa Xaa Xaa Xaa Xaa Xaa Xaa Xaa Xaa Xaa Xaa Xaa
            915                 920                 925

Xaa Xaa Xaa Xaa Xaa Xaa Xaa Xaa Xaa Xaa Xaa Xaa Xaa Xaa Xaa
            930                 935                 940

Xaa Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Xaa Xaa Xaa Xaa
            965                 970                 975

Xaa Xaa Xaa Xaa Xaa Xaa Xaa Xaa Xaa Xaa Xaa Xaa Xaa Xaa Xaa
            980                 985                 990

Xaa Xaa Xaa Xaa Xaa Xaa Xaa Xaa Xaa Xaa Xaa Xaa Xaa Xaa Xaa
            995                 1000                1005

Xaa Xaa Xaa Xaa Xaa Xaa Xaa Xaa Xaa Xaa Xaa Xaa Xaa Xaa Xaa
            1010                1015                1020

Xaa Xaa Xaa Xaa Xaa Xaa Xaa Xaa Xaa Xaa Xaa Xaa Xaa Xaa Xaa Xaa
1025                1030                1035                1040

Xaa Xaa Xaa Xaa Xaa Xaa Xaa Xaa Xaa Xaa Xaa Xaa Xaa Xaa Xaa
            1045                1050                1055

Xaa Xaa Xaa Xaa Xaa Xaa Xaa Xaa Xaa Xaa Xaa Xaa Xaa Xaa Xaa
            1060                1065                1070

Xaa Xaa Xaa Xaa Xaa Xaa Xaa Xaa Xaa Xaa Xaa Xaa Xaa Xaa Xaa
            1075                1080                1085

Xaa Xaa Xaa Xaa Xaa Xaa Xaa Xaa Xaa Xaa Xaa Xaa Xaa Xaa Xaa
            1090                1095                1100

Xaa Xaa Xaa Xaa Xaa Xaa Xaa Xaa Xaa Xaa Xaa Xaa Xaa Xaa Xaa Xaa
1105                1110                1115                1120

Xaa Xaa Xaa Xaa Xaa Xaa Xaa Xaa Xaa Xaa Xaa Xaa Xaa Xaa Xaa
            1125                1130                1135

Xaa Xaa Xaa Xaa Xaa Xaa Xaa Xaa Xaa Xaa Xaa Xaa Xaa Xaa Xaa
            1140                1145                1150

Xaa Xaa Xaa Xaa Xaa Xaa Xaa Xaa Xaa Xaa Xaa Xaa Xaa Xaa Xaa
            1155                1160                1165

Xaa Xaa Xaa Xaa Xaa Xaa Xaa Xaa Xaa Xaa Xaa Xaa Xaa Xaa Xaa
            1170                1175                1180

Xaa Xaa Xaa Xaa Xaa Xaa Xaa Xaa Xaa Xaa Xaa Xaa Xaa Xaa Xaa Xaa
1185                1190                1195                1200

Xaa Xaa Xaa Xaa Xaa Xaa Xaa Xaa Xaa Xaa Xaa Xaa Xaa Xaa Xaa
            1205                1210                1215

Xaa Xaa Xaa Xaa Xaa Xaa Xaa Xaa Xaa Xaa Xaa Xaa Xaa Xaa Xaa
            1220                1225                1230

Xaa Xaa Xaa Xaa Xaa Xaa Xaa Xaa Xaa Xaa Xaa Xaa Xaa Xaa Xaa
            1235                1240                1245

Xaa Xaa Xaa Xaa Xaa Xaa Xaa Xaa Xaa Xaa Xaa Xaa Xaa Xaa Xaa
            1250                1255                1260

Xaa Xaa Xaa Xaa Xaa Xaa Xaa Xaa Xaa Xaa Xaa Xaa Xaa Xaa Xaa Xaa
1265                1270                1275                1280

```
Xaa Xaa Xaa Xaa Xaa Xaa Xaa Xaa Xaa Xaa Xaa Xaa Xaa Xaa Xaa
            1285                1290                1295

Xaa Xaa Xaa Xaa Xaa Xaa Xaa Xaa Xaa Xaa Xaa Xaa Xaa Xaa Xaa
            1300                1305                1310

Xaa Xaa Xaa Xaa Xaa Xaa Xaa Xaa Xaa Xaa Xaa Xaa Xaa Xaa Xaa
        1315                1320                1325

Xaa Xaa Xaa Xaa Xaa Xaa Xaa Xaa Xaa Xaa Xaa Xaa Xaa Xaa Xaa
        1330                1335                1340

Xaa Xaa Xaa Xaa Xaa Xaa Xaa Xaa Xaa Xaa Xaa Xaa Xaa Xaa Xaa
1345                1350                1355                1360

Xaa Xaa Xaa Xaa Xaa Xaa Xaa Xaa Xaa Xaa Xaa Xaa Xaa Xaa Xaa
            1365                1370                1375

Xaa Xaa Xaa Xaa Xaa Xaa Xaa Xaa Xaa Xaa Xaa Xaa Xaa Xaa Xaa
            1380                1385                1390

Xaa Xaa Xaa Xaa Xaa Xaa Xaa Xaa Xaa Xaa Xaa Xaa Xaa Xaa Xaa
        1395                1400                1405

Xaa Xaa Xaa Xaa Xaa Xaa Xaa Xaa Xaa Xaa Xaa Xaa Xaa Xaa Xaa
        1410                1415                1420

Xaa Xaa Xaa Xaa Xaa Xaa Xaa Xaa Xaa Xaa Xaa Xaa Xaa Xaa Xaa
1425                1430                1435                1440

Xaa Xaa Xaa Xaa Xaa Xaa Xaa Xaa Xaa Xaa Xaa Xaa Xaa Xaa Xaa
            1445                1450                1455

Xaa Xaa Xaa Xaa Xaa Xaa Xaa Xaa Xaa Xaa Xaa Xaa Xaa Xaa Xaa
            1460                1465                1470

Xaa Xaa Xaa Xaa Xaa Xaa Xaa Xaa Xaa Xaa Xaa Xaa Xaa Xaa Xaa
        1475                1480                1485

Xaa Xaa Xaa Xaa Xaa Xaa Xaa Xaa Xaa Xaa Xaa Xaa Xaa Xaa Xaa
        1490                1495                1500

Xaa Xaa Xaa Xaa Xaa Xaa Xaa Xaa Xaa Xaa Xaa Xaa Xaa Xaa Xaa
1505                1510                1515                1520

Xaa Xaa Xaa Xaa Xaa Xaa Xaa Xaa Xaa Xaa Xaa Xaa Xaa Xaa Xaa
            1525                1530                1535

Xaa Xaa Xaa Xaa Xaa Xaa Xaa Xaa Xaa Xaa Xaa Xaa Xaa Xaa Xaa
            1540                1545                1550

Xaa Xaa Xaa Xaa Xaa Xaa Xaa Xaa Xaa Xaa Xaa Xaa Xaa Xaa Xaa
        1555                1560                1565

Xaa Xaa Xaa Xaa Xaa Xaa Xaa Xaa Xaa Xaa Xaa Xaa Xaa Xaa Xaa
        1570                1575                1580

Xaa Xaa Xaa Xaa Xaa Xaa Xaa Xaa Xaa Xaa Xaa Xaa Xaa Xaa Xaa
1585                1590                1595                1600

Xaa Xaa Xaa Xaa Xaa Xaa Xaa Xaa Xaa Xaa Xaa Xaa Xaa Xaa Xaa
            1605                1610                1615

Xaa Xaa Xaa Xaa Xaa Xaa Xaa Xaa Xaa Xaa Xaa Xaa Xaa Xaa Xaa
            1620                1625                1630

Xaa Xaa Xaa Xaa Xaa Xaa Xaa Xaa Xaa Xaa Xaa Xaa Xaa Xaa Xaa
        1635                1640                1645

Xaa Xaa Xaa Xaa Xaa Xaa Xaa Xaa Xaa Xaa Xaa Xaa Xaa Xaa Xaa
        1650                1655                1660

Xaa Xaa Xaa Xaa Xaa Xaa Xaa Xaa Xaa Xaa Xaa Xaa Xaa Xaa Xaa
1665                1670                1675                1680

Xaa Xaa Xaa Xaa Xaa Xaa Xaa Xaa Xaa Xaa Xaa Xaa Xaa Xaa Xaa
            1685                1690                1695

Xaa Xaa Xaa Xaa Xaa Xaa Xaa Xaa Xaa Xaa Xaa Xaa Xaa Xaa Xaa
```

-continued

```
                    1700                1705                1710

Xaa Xaa Xaa Xaa Xaa Xaa Xaa Xaa Xaa Xaa Xaa Xaa Xaa Xaa Xaa
            1715                1720                1725

Xaa Xaa Xaa Xaa Xaa Xaa Xaa Xaa Xaa Xaa Xaa Xaa Xaa Xaa Xaa
            1730                1735                1740

Xaa Xaa Xaa Xaa Xaa Xaa Xaa Xaa Xaa Xaa

-continued

Xaa Xaa Xaa Xaa Xaa Xaa Xaa Xaa Xaa Xaa Xaa Xaa Xaa Xaa Xaa
                2130                2135                2140

Xaa Xaa Xaa Xaa Xaa Xaa Xaa Xaa Xaa Xaa Xaa Xaa Xaa Xaa Cys Xaa
2145                2150                2155                2160

Xaa Xaa Xaa Xaa Xaa Xaa Xaa Xaa Xaa Xaa Xaa Xaa Xaa Xaa Xaa
                2165                2170                2175

Xaa Xaa Xaa Xaa Xaa Xaa Xaa Xaa Xaa Xaa Xaa Xaa Xaa Xaa Xaa
                2180                2185                2190

Xaa Xaa Xaa Xaa Xaa Xaa Xaa Xaa Xaa Xaa Xaa Xaa Xaa Xaa Xaa
                2195                2200                2205

Xaa Xaa Xaa Xaa Xaa Xaa Xaa Xaa Xaa Xaa Xaa Xaa Xaa Xaa Xaa
                2210                2215                2220

Xaa Xaa Xaa Xaa Xaa Xaa Xaa Xaa Xaa Xaa Xaa Xaa Xaa Xaa Xaa Xaa
2225                2230                2235                2240

Xaa Xaa Xaa Xaa Xaa Xaa Xaa Xaa Xaa Xaa Xaa Xaa Xaa Xaa Xaa
                2245                2250                2255

Xaa Xaa Xaa Cys Xaa Xaa Xaa Xaa Xaa Xaa Xaa Xaa Xaa Xaa Xaa
                2260                2265                2270

Xaa Xaa Xaa Xaa Xaa Xaa Xaa Xaa Xaa Xaa Xaa Xaa Xaa Xaa Xaa
                2275                2280                2285

Xaa Xaa Xaa Xaa Xaa Xaa Xaa Xaa Xaa Xaa Xaa Xaa Xaa Xaa Xaa
                2290                2295                2300

Xaa Xaa Xaa Xaa Xaa Xaa Cys Xaa Xaa Xaa Xaa Xaa Cys Xaa Xaa Xaa
2305                2310                2315                2320

Xaa Xaa Xaa Xaa Xaa Xaa Xaa Xaa Xaa Xaa Xaa Xaa Xaa Xaa Xaa
                2325                2330                2335

Xaa Xaa Xaa Xaa Xaa Xaa Xaa Xaa Xaa Xaa Xaa Xaa Xaa Xaa Xaa
                2340                2345                2350

Xaa Xaa Xaa Xaa Xaa Xaa Xaa Xaa Xaa Xaa Xaa Xaa Xaa Xaa Cys
                2355                2360                2365

Xaa Xaa Xaa Xaa Xaa Xaa Xaa Xaa Xaa Xaa Xaa Xaa Xaa Xaa Xaa
                2370                2375                2380

Xaa Xaa Xaa Xaa Xaa Xaa Xaa Xaa Xaa Xaa Xaa Xaa Xaa Xaa Xaa Xaa
2385                2390                2395                2400

Xaa Xaa Xaa Xaa Xaa Xaa Xaa Xaa Xaa Xaa Xaa Xaa Xaa Xaa Xaa
                2405                2410                2415

Xaa Xaa Xaa Xaa Xaa Xaa Xaa Xaa Xaa Xaa Xaa Xaa Xaa Xaa Xaa
                2420                2425                2430

Xaa Xaa Xaa Xaa Xaa Xaa Xaa Xaa Xaa Xaa Xaa Xaa Xaa Xaa Xaa
                2435                2440                2445

Xaa Xaa Xaa Xaa Xaa Xaa Xaa Xaa Xaa Xaa Xaa Xaa Xaa Xaa Xaa
                2450                2455                2460

Xaa Xaa Xaa Xaa Xaa Xaa Xaa Xaa Xaa Xaa Xaa Xaa Xaa Xaa Xaa Xaa
2465                2470                2475                2480

Xaa Xaa Xaa Xaa Xaa Xaa Xaa Xaa Xaa Xaa Xaa Xaa Xaa Xaa Xaa
                2485                2490                2495

Xaa Xaa Xaa Xaa Xaa Xaa Xaa Xaa Xaa Xaa Xaa Xaa Xaa Xaa Xaa
                2500                2505                2510

Xaa Xaa Xaa Xaa Xaa Xaa Xaa Xaa Xaa Xaa Xaa Xaa Xaa Xaa Xaa
                2515                2520                2525

Xaa Xaa Xaa Xaa Xaa Xaa Xaa Xaa Xaa Xaa Xaa Xaa Xaa Xaa Xaa
                2530                2535                2540

-continued

```
Xaa Xaa Xaa Xaa Xaa Xaa Xaa Xaa Xaa Xaa Xaa Xaa Xaa Xaa Xaa
2545                2550                2555                2560

Xaa Xaa Xaa Xaa Xaa Xaa Xaa Xaa Xaa Xaa Xaa Xaa Xaa Xaa Xaa
            2565                2570                2575

Xaa Xaa Xaa Xaa Xaa Xaa Xaa Xaa Xaa Xaa Xaa Xaa Xaa Xaa Xaa
        2580                2585                2590

Xaa Xaa Xaa Xaa Xaa Xaa Xaa Xaa Xaa Xaa Xaa Xaa Xaa Xaa Xaa
    2595                2600                2605

Xaa Xaa Xaa Xaa Xaa Xaa Xaa Xaa Xaa Xaa Xaa Xaa Xaa Xaa Xaa
            2610                2615                2620

Xaa Xaa Xaa Xaa Xaa Xaa Xaa Xaa Xaa Xaa Xaa Xaa Xaa Xaa Xaa
2625                2630                2635                2640

Xaa Xaa Xaa Xaa Xaa Xaa Xaa Xaa Xaa Xaa Xaa Xaa Xaa Xaa Xaa
            2645                2650                2655

Xaa Xaa Xaa Xaa Xaa Xaa Xaa Xaa Xaa Xaa Xaa Xaa Xaa Xaa Xaa
        2660                2665                2670

Xaa Xaa Xaa Xaa Xaa Xaa Xaa Xaa Xaa Xaa Xaa Xaa Xaa Xaa Xaa
    2675                2680                2685

Xaa Xaa Xaa Xaa Xaa Xaa Xaa Xaa Xaa Xaa Xaa Xaa Xaa Xaa Xaa
            2690                2695                2700

Xaa Xaa Xaa Xaa Xaa Xaa Xaa Xaa Xaa Xaa Xaa Xaa Xaa Xaa Xaa
2705                2710                2715                2720

Xaa Xaa Xaa Xaa Xaa Xaa Xaa Xaa Xaa Xaa Xaa Xaa Xaa Xaa Xaa
            2725                2730                2735

Xaa Xaa Xaa Xaa Xaa Xaa Xaa Xaa Xaa Xaa Xaa Xaa Xaa Xaa Xaa
        2740                2745                2750

Xaa Xaa Xaa Xaa Xaa Xaa Xaa Xaa Xaa Xaa Xaa Xaa Xaa Xaa Xaa
    2755                2760                2765

Xaa Xaa Xaa Xaa Xaa Xaa Xaa Xaa Xaa Xaa Xaa Xaa Xaa Xaa Xaa
            2770                2775                2780

Xaa Xaa Xaa Xaa Xaa Xaa Xaa Xaa Xaa Xaa Xaa Xaa Xaa Xaa Xaa
2785                2790                2795                2800

Xaa Xaa Xaa Xaa Xaa Xaa Xaa Xaa Xaa Xaa Xaa Xaa Xaa Xaa Xaa
            2805                2810                2815

Xaa Xaa Xaa Xaa Xaa Xaa Xaa Xaa Xaa Xaa Xaa Xaa Xaa Xaa Xaa
        2820                2825                2830

Xaa Xaa Xaa Xaa Xaa Xaa Xaa Xaa Xaa Xaa Xaa Xaa Xaa Xaa Xaa
    2835                2840                2845

Xaa Xaa Xaa Xaa Xaa Xaa Xaa Xaa Xaa Xaa Xaa Xaa Xaa Xaa Xaa
            2850                2855                2860

Xaa Xaa Xaa Xaa Xaa Xaa Xaa Xaa Xaa Xaa Xaa Xaa Xaa Xaa Xaa
2865                2870                2875                2880

Xaa Xaa Xaa Xaa Xaa Xaa Xaa Xaa Xaa Xaa Xaa Xaa Xaa Xaa Xaa
            2885                2890                2895

Xaa Xaa Xaa Xaa Xaa Xaa Xaa Xaa Xaa Xaa Xaa Xaa Xaa Xaa Xaa
        2900                2905                2910

Xaa Xaa Xaa Xaa Xaa Xaa Xaa Xaa Xaa Xaa Xaa Xaa Xaa Xaa Xaa
    2915                2920                2925

Xaa Xaa Xaa Xaa Xaa Xaa Xaa Xaa Xaa Xaa Xaa Xaa Xaa Xaa Xaa
            2930                2935                2940

Xaa Xaa Xaa Xaa Xaa Xaa Xaa Xaa Xaa Xaa Xaa Xaa Xaa Xaa Xaa
2945                2950                2955                2960

Xaa Xaa Xaa Xaa Xaa Xaa Xaa Xaa Xaa Xaa Xaa Xaa Xaa Xaa Xaa
```

-continued

Xaa Xaa Xaa Xaa Xaa Xaa Xaa Xaa Xaa Xaa Xaa Xaa Xaa Xaa Xaa
            2965                2970                2975

Xaa Xaa Xaa Xaa Xaa Xaa Xaa Xaa Xaa Xaa Xaa Xaa Xaa Xaa Xaa
        2980                2985                2990

Xaa Xaa Xaa Xaa Xaa Xaa Xaa Xaa Xaa Xaa Xaa Xaa Xaa Xaa Xaa
    2995                3000                3005

Xaa Xaa Xaa Xaa Xaa Xaa Xaa Xaa Xaa Xaa Xaa Xaa Xaa Xaa Xaa
 3010                3015                3020

Xaa Xaa Xaa Xaa Xaa Xaa Xaa Xaa Xaa Xaa Xaa Xaa Xaa Xaa Xaa
3025                3030                3035                3040

Xaa Xaa Xaa Xaa Xaa Xaa Xaa Xaa Xaa Xaa Xaa Xaa Xaa Xaa Xaa
            3045                3050                3055

Xaa Xaa Xaa Xaa Xaa Xaa Xaa Xaa Xaa Xaa Xaa Xaa Xaa Xaa Xaa
        3060                3065                3070

Xaa Xaa Xaa Xaa Xaa Xaa Xaa Xaa Xaa Xaa Xaa Xaa Xaa Xaa Xaa
    3075                3080                3085

Xaa Xaa Xaa Xaa Xaa Xaa Xaa Xaa Xaa Xaa Xaa Xaa Xaa Xaa Xaa
 3090                3095                3100

Xaa Xaa Xaa Xaa Xaa Xaa Xaa Xaa Xaa Xaa Xaa Xaa Xaa Xaa Xaa
3105                3110                3115                3120

Xaa Xaa Xaa Xaa Xaa Xaa Xaa Xaa Xaa Xaa Xaa Xaa Xaa Xaa Xaa
            3125                3130                3135

Xaa Xaa Xaa Xaa Xaa Xaa Xaa Xaa Xaa Xaa Xaa Xaa Xaa Xaa Xaa
        3140                3145                3150

Xaa Xaa Xaa Xaa Xaa Xaa Xaa Xaa Xaa Xaa Xaa Xaa Xaa Xaa Xaa
    3155                3160                3165

Xaa Xaa Xaa Xaa Xaa Xaa Xaa Xaa Xaa Xaa Xaa Xaa Xaa Xaa Xaa
 3170                3175                3180

Xaa Xaa Xaa Xaa Xaa Xaa Xaa Xaa Xaa Xaa Xaa Xaa Xaa Xaa Xaa
3185                3190                3195                3200

Xaa Xaa Xaa Xaa Xaa Xaa Xaa Xaa Xaa Xaa Xaa Xaa Xaa Xaa Xaa
            3205                3210                3215

Xaa Xaa Xaa Xaa Xaa Xaa Xaa Xaa Xaa Xaa Xaa Xaa Xaa Xaa Xaa
        3220                3225                3230

Xaa Xaa Xaa Xaa Xaa Xaa Xaa Xaa Xaa Xaa Xaa Xaa Xaa Xaa Xaa
    3235                3240                3245

Xaa Xaa Xaa Xaa Xaa Xaa Xaa Xaa Xaa Xaa Xaa Xaa Xaa Xaa Xaa
 3250                3255                3260

Xaa Xaa Xaa Xaa Xaa Xaa Xaa Xaa Xaa Xaa Xaa Xaa Xaa Xaa Xaa
3265                3270                3275                3280

Xaa Xaa Xaa Xaa Xaa Xaa Xaa Xaa Xaa Xaa Xaa Xaa Xaa Xaa Xaa
            3285                3290                3295

Xaa Xaa Xaa Xaa Xaa Xaa Xaa Xaa Xaa Xaa Xaa Xaa Xaa Xaa Xaa
        3300                3305                3310

Xaa Xaa Xaa Xaa Xaa Xaa Xaa Xaa Xaa Xaa Xaa Xaa Xaa Xaa Xaa
    3315                3320                3325

Xaa Xaa Xaa Xaa Xaa Xaa Xaa Xaa Xaa Xaa Xaa Xaa Xaa Xaa Xaa
 3330                3335                3340

Xaa Xaa Xaa Xaa Xaa Xaa Xaa Xaa Xaa Xaa Xaa Xaa Xaa Xaa Xaa
3345                3350                3355                3360

Xaa Xaa Xaa Xaa Xaa Xaa Xaa Xaa Xaa Xaa Xaa Xaa Xaa Xaa Xaa
            3365                3370                3375

Xaa Xaa Xaa Xaa Xaa Xaa Xaa Xaa Xaa Xaa Xaa Xaa Xaa Xaa Xaa
        3380                3385                3390

-continued

```
Xaa Xaa Xaa Xaa Xaa Xaa Xaa Xaa Xaa Xaa Xaa Xaa Xaa Xaa Xaa
            3395                3400                3405

Xaa Xaa Xaa Xaa Xaa Xaa Xaa Xaa Xaa Xaa Xaa Xaa Xaa Xaa Xaa
        3410                3415                3420

Xaa Xaa Xaa Xaa Xaa Xaa Xaa Xaa Xaa Xaa Xaa Xaa Xaa Xaa Xaa
3425                3430                3435                3440

Xaa Xaa Xaa Xaa Xaa Xaa Xaa Xaa Xaa Xaa Xaa Xaa Xaa Xaa Xaa
            3445                3450                3455

Xaa Xaa Xaa Xaa Xaa Xaa Xaa Xaa Xaa Xaa Xaa Xaa Xaa Xaa Xaa
        3460                3465                3470

Xaa Xaa Xaa Xaa Xaa Xaa Xaa Xaa Xaa Xaa Xaa Xaa Xaa Xaa Xaa
    3475                3480                3485

Xaa Xaa Xaa Xaa Xaa Xaa Xaa Xaa Xaa Xaa Xaa Xaa Xaa Xaa Xaa
3490                3495                3500

Xaa Xaa Xaa Xaa Xaa Xaa Xaa Xaa Xaa Xaa Xaa Xaa Xaa Xaa Xaa
3505                3510                3515                3520

Xaa Xaa Xaa Xaa Xaa Xaa Xaa Xaa Xaa Xaa Xaa Xaa Xaa Xaa Xaa
            3525                3530                3535

Xaa Xaa Xaa Xaa Xaa Xaa Xaa Xaa Xaa Xaa Xaa Xaa Xaa Xaa Xaa
        3540                3545                3550

Xaa Xaa Xaa Xaa Xaa Xaa Xaa Xaa Xaa Xaa Xaa Xaa Xaa Xaa Xaa
    3555                3560                3565

Xaa Xaa Xaa Xaa Xaa Xaa Xaa Xaa Xaa Xaa Xaa Xaa Xaa Xaa Xaa
3570                3575                3580

Xaa Xaa Xaa Xaa Xaa Xaa Xaa Xaa Xaa Xaa Xaa Xaa Xaa Xaa Xaa
3585                3590                3595                3600

Xaa Xaa Xaa Xaa Xaa Xaa Xaa Xaa Xaa Xaa Xaa Xaa Xaa Xaa Xaa
            3605                3610                3615

Xaa Xaa Xaa Xaa Xaa Xaa Xaa Xaa Xaa Xaa Xaa Xaa Xaa Xaa Xaa
        3620                3625                3630

Xaa Xaa Xaa Xaa Xaa Xaa Xaa Xaa Xaa Xaa Xaa Xaa Xaa Xaa Xaa
    3635                3640                3645

Xaa Xaa Xaa Xaa Xaa Xaa Xaa Xaa Xaa Xaa Xaa Xaa Xaa Xaa Xaa
3650                3655                3660

Xaa Xaa Xaa Xaa Xaa Xaa Xaa Xaa Xaa Xaa Xaa Xaa Xaa Xaa Xaa
3665                3670                3675                3680

Xaa Xaa Xaa Xaa Xaa Xaa Xaa Xaa Xaa Xaa Xaa Xaa Xaa Xaa Xaa
            3685                3690                3695

Xaa Xaa Xaa Xaa Xaa Xaa Xaa Xaa Xaa Xaa Xaa Xaa Xaa Xaa Xaa
        3700                3705                3710

Xaa Xaa Xaa Xaa Xaa Xaa Xaa Xaa Xaa Xaa Xaa Xaa Xaa Xaa Xaa
    3715                3720                3725

Xaa Xaa Xaa Xaa Xaa Xaa Xaa Xaa Xaa Xaa Xaa Xaa Xaa Xaa Xaa
3730                3735                3740

Xaa Xaa Xaa Xaa Xaa Xaa Xaa Xaa Xaa Xaa Xaa Xaa Xaa Xaa Xaa
3745                3750                3755                3760

Xaa Xaa Xaa Xaa Xaa Xaa Xaa Xaa Xaa Xaa Xaa Xaa Xaa Xaa Xaa
            3765                3770                3775

Xaa Xaa Xaa Xaa Xaa Xaa Xaa Xaa Xaa Xaa Xaa Xaa Xaa Xaa Xaa
        3780                3785                3790

Xaa Xaa Xaa Xaa Xaa Xaa Xaa Xaa Xaa Xaa Xaa Xaa Xaa Xaa Xaa
    3795                3800                3805
```

```
Xaa Xaa Xaa Xaa Xaa Xaa Xaa Xaa Xaa Xaa Xaa Xaa Xaa Xaa Xaa
    3810            3815            3820

Xaa Xaa Xaa Xaa Xaa Xaa Xaa Xaa Xaa Xaa Xaa Xaa Xaa Xaa Xaa
3825            3830            3835            3840

Xaa Xaa Xaa Xaa Xaa Xaa Xaa Xaa Xaa Xaa Xaa Xaa Xaa Xaa Xaa
        3845            3850            3855

Xaa Xaa Xaa Xaa Xaa Xaa Xaa Xaa Xaa Xaa Xaa Xaa Xaa Xaa Xaa
    3860            3865            3870

Xaa Xaa Xaa Xaa Xaa Xaa Xaa Xaa Xaa Xaa Xaa Xaa Xaa Xaa Xaa
        3875            3880            3885

Xaa Xaa Xaa Xaa Xaa Xaa Xaa Xaa Xaa Xaa Xaa Xaa Xaa Xaa Xaa
    3890            3895            3900

Xaa Xaa Xaa Xaa Xaa Xaa Xaa Xaa Xaa Xaa Xaa Xaa Xaa Xaa Xaa
3905            3910            3915            3920

Xaa Xaa Xaa Xaa Xaa Xaa Xaa Xaa Xaa Xaa Xaa Xaa Xaa Xaa Xaa
        3925            3930            3935

Xaa Xaa Xaa Xaa Xaa Xaa Xaa Xaa Xaa Xaa Xaa Xaa Xaa Xaa Xaa
    3940            3945            3950

Xaa Xaa Xaa Xaa Xaa Xaa Xaa Xaa Xaa Xaa Xaa Xaa Xaa Xaa Xaa
        3955            3960            3965

Xaa Xaa Xaa Xaa Xaa Xaa Xaa Xaa Xaa Xaa Xaa Xaa Xaa Xaa Xaa
    3970            3975            3980

Xaa Xaa Xaa Xaa Xaa Xaa Xaa Xaa Xaa Xaa Xaa Xaa Xaa Xaa Xaa
3985            3990            3995            4000

Xaa Xaa Xaa Xaa Xaa Xaa Xaa Xaa Xaa Xaa Xaa Xaa Xaa Xaa Xaa
        4005            4010            4015

Xaa Xaa Xaa Xaa Xaa Xaa Xaa Xaa Xaa Xaa Xaa Xaa Xaa Xaa Xaa
    4020            4025            4030

Xaa Xaa Xaa Xaa Xaa Xaa Xaa Xaa Xaa Xaa Xaa Xaa Xaa Xaa Xaa
        4035            4040            4045

Xaa Xaa Xaa Xaa Xaa Xaa Xaa Xaa Xaa Xaa Xaa Xaa Xaa Xaa Xaa
    4050            4055            4060

Xaa Xaa Xaa Xaa Xaa Xaa Xaa Xaa Xaa Xaa Xaa Xaa Xaa Xaa Xaa
4065            4070            4075            4080

Xaa Xaa Xaa Xaa Xaa Xaa Xaa Xaa Xaa Xaa Xaa Xaa Xaa Xaa Xaa
        4085            4090            4095

Xaa Xaa Xaa Xaa Xaa Xaa Xaa Xaa Xaa Xaa Xaa Xaa Xaa Xaa Xaa
    4100            4105            4110

Xaa Xaa Xaa Xaa Xaa Xaa Xaa Xaa Xaa Xaa Xaa Xaa Xaa Xaa Xaa
        4115            4120            4125

Xaa Xaa Xaa Xaa Xaa Xaa Xaa Xaa Xaa Xaa Xaa Xaa Xaa Xaa Xaa
    4130            4135            4140

Xaa Xaa Xaa Xaa Xaa Xaa Xaa Xaa Xaa Xaa Xaa Xaa Xaa Xaa Xaa
4145            4150            4155            4160

Xaa Xaa Xaa Xaa Xaa Xaa Xaa Xaa Xaa Xaa Xaa Xaa Xaa Xaa Xaa
        4165            4170            4175

Xaa Xaa Xaa Xaa Xaa Xaa Xaa Xaa Xaa Xaa Xaa Xaa Xaa Xaa Xaa
    4180            4185            4190

Xaa Xaa Xaa Xaa Xaa Xaa Xaa Xaa Xaa Xaa Xaa Xaa Xaa Xaa Xaa
        4195            4200            4205

Xaa Xaa Xaa Xaa Xaa Xaa Xaa Xaa Xaa Xaa Xaa Xaa Xaa Xaa Xaa
    4210            4215            4220

Xaa Xaa Xaa Xaa Xaa Xaa Xaa Xaa Xaa Xaa Xaa Xaa Xaa Xaa Xaa
```

```
4225                4230                4235                4240
Xaa Xaa Xaa Xaa Xaa Xaa Xaa Xaa Xaa Xaa Xaa Xaa Xaa Xaa Xaa Xaa
                4245                4250                4255
Xaa Xaa Xaa Xaa Xaa Xaa Xaa Xaa Xaa Xaa Xaa Xaa Xaa Xaa Xaa Xaa
                4260                4265                4270
Xaa Xaa Xaa Xaa Xaa Xaa Xaa Xaa Xaa Xaa Xaa Xaa Xaa Xaa Xaa Xaa
            4275                4280                4285
Xaa Xaa Xaa Xaa Xaa Xaa Xaa Xaa Xaa Xaa Xaa Xaa Xaa Xaa Xaa Xaa
        4290                4295                4300
Xaa Xaa Xaa Xaa Xaa Xaa Xaa Xaa Xaa Xaa Xaa Xaa Xaa Xaa Xaa Xaa
4305                4310                4315                4320
Xaa Xaa Xaa Xaa Xaa Xaa Xaa Xaa Xaa Xaa Xaa Xaa Xaa Xaa Xaa Xaa
                4325                4330                4335
Xaa Xaa Xaa Xaa Xaa Xaa Xaa Xaa Xaa Xaa Xaa Xaa Xaa Xaa Xaa Xaa
                4340                4345                4350
Xaa Xaa Xaa Xaa Xaa Xaa Xaa Xaa Xaa Xaa Xaa Xaa Xaa Xaa Xaa Xaa
            4355                4360                4365
```